United States Patent
Amano et al.

(10) Patent No.: US 8,772,044 B2
(45) Date of Patent: Jul. 8, 2014

(54) METHOD OF NEGATIVE-ION MALDI ANALYSIS OF NEUTRAL LABELED SUGARS AND SCREENING DISEASE MARKERS

(75) Inventors: Junko Amano, Tokyo (JP); Koichi Tanaka, Kyoto (JP)

(73) Assignees: The Noguchi Institute, Tokyo (JP); Shimadzu Corporation, Kyoto (JP)

( * ) Notice: Subject to any disclaimer, the term of this patent is extended or adjusted under 35 U.S.C. 154(b) by 1668 days.

(21) Appl. No.: 11/887,365

(22) PCT Filed: Mar. 27, 2006

(86) PCT No.: PCT/JP2006/306981
§ 371 (c)(1),
(2), (4) Date: Sep. 27, 2007

(87) PCT Pub. No.: WO2006/106997
PCT Pub. Date: Oct. 12, 2006

(65) Prior Publication Data
US 2009/0250604 A1     Oct. 8, 2009

(30) Foreign Application Priority Data

Mar. 31, 2005   (JP) .................................. 2005-101536
Mar. 31, 2005   (JP) .................................. 2005-101537

(51) Int. Cl.
*G01N 33/00*     (2006.01)

(52) U.S. Cl.
USPC .......................................... 436/95; 436/173

(58) Field of Classification Search
CPC .............. G01N 2560/00; G01N 30/72; G01N 33/5308; A61K 39/0011
See application file for complete search history.

(56) References Cited

U.S. PATENT DOCUMENTS

| | | | |
|---|---|---|---|
| 7,951,603 B2 | 5/2011 | Amano | |
| 2004/0137557 A1 | 7/2004 | DeFrees et al. | |

FOREIGN PATENT DOCUMENTS

| | | |
|---|---|---|
| JP | 2004-073012 A | 3/2004 |
| JP | 2004-317398 A | 11/2004 |
| WO | WO 2004/092739 A1 | 10/2004 |

OTHER PUBLICATIONS

Anumula and Dhume, "High resolution and high sensitivity methods for oligosaccharide mapping and characterization by normal phase high performance liquid chromatography following derivatization with highly fluorescent anthranilic acid", Glycobiology, 1998, v. 8, No. 7, pp. 685-694.*

(Continued)

*Primary Examiner* — Yelena G Gakh
(74) *Attorney, Agent, or Firm* — Cheng Law Group, PLLC

(57) ABSTRACT

The present invention provides a method for obtaining structural information conveniently and rapidly by generating a negative ion without adding an acidic substance to matrix, thereby improving sensitivity of measurement by a mass spectrometer, and by generating structural specific ions with high reproducibility, and a method for screening disease marker and a method for analyzing a sample containing a biomolecule. A method for mass spectrometry of a sugar chain comprising the steps of: preparing a sample containing a sugar chain; labeling the sugar chain with a labeling compound, to obtain a labeled sugar chain; and subjecting the labeled sugar chain to measurement of negative ions by using a MALDI mass spectrometer, thereby conducting analysis of the sugar chain. A method for screening disease marker comprising the steps of: (1) labeling the biomolecule X derived from a subject affected by a particular disease; subjecting the labeled biomolecule X' to measurement of negative ions by a MALDI mass spectrometer, (2) separately, labeling the biomolecule Y derived from a subject unaffected by the particular disease; subjecting the labeled biomolecule Y' to measurement of negative ions by a MALDI mass spectrometer; and (3) comparing mass spectrum of the labeled biomolecule X' obtained in (1) with mass spectrum of the labeled biomolecule Y' obtained in (2) to find mass spectrum peaks which are mutually different, thereby ascertaining presence of structure involved in expression of the particular disease.

20 Claims, 7 Drawing Sheets

(56) References Cited

OTHER PUBLICATIONS

Joo An (Hyun Joo An et al). "Improved capillary electrophoretic separation and mass spectrometric detection of oligosaccharides", Journal of Chromatography A, 2003, v.1004, pp. 121-129.*

Amano et al. "Negative-ion MALDI-QIT-TOFMSn for structural determination of fucosylated and sialylated oligosaccharides labeled with a pyrene derivative", Glycobiology, 2009, vol. 19, No. 6, pp. 592-600.*

Supplementary Partial European Search Report for the Application No. EP 06 73 0929 dated Feb. 12, 2009.

Suzuki, Hirofumi et al., "Analysis of 1-Aminopyrene-3,6,8-trisulfonate-Derivatized Oligosaccharides by Capillary Electrophoresis with Matrix-Assisted Laser Desorption/Ionization Time-of-Flight Mass Spectrometry", Analytical Chemistry, Nov. 1997, vol. 69, No. 22, pp. 4554-4559.

Perreault, Helene et al., "Stereochemical Effects on the Mass Spectrometric Behavior of Native and Derivatized Trisaccharide Isomers: Comparisons with Results from Molecular Modeling", Journal of Mass Spectrometry, 1999, vol. 34, pp. 184-197.

Wong, Anissa W. et al., "Selection of Anionic Dopant for Quantifying Desialylation Reactions with MALDI-FTMS", Analytical Chemistry, Apr. 2000, vol. 72, No. 7, pp. 1419-1425.

Lemoine, Jerome et al., "Analysis of 8-aminonaphthalene-1,3,6-trisulfonic acid labelled N-glycans by matrix-assisted laser desorption/ionisation time-of-flight mass spectrometry", Rapid Communications in Mass Spectrometry, 2000, vol. 14, pp. 100-104.

Yamagaki, Tohru et al., "Ion intensity analysis of post-source decay fragmentation in curved-field reflectron matrix-assisted laser desorption/ionization time-of-flight mass spectrometry of carbohydrates: For structural characterization of glycosylation in proteome analysis", Proteomics, 2001, vol. 1, pp. 329-339.

Cai, Yang et al., "Anionic Adducts of Oligosaccharides by Matrix-Assisted Laser Desorption/Ionization Time-of-Flight Mass Spectrometry", Analytical Chemistry, Apr. 2003, vol. 75, No. 7, pp. 1638-1644.

Wuhrer, Manfred et al., "Negative-Mode MALDI-TOF/TOF-MS of Oligosaccharides Labeled with 2-Aminobenzamide", Analytical Chemistry, Nov. 2005, vol. 77, No. 21, pp. 6954-6959.

Harvey, David J., "Structural determination of N-linked glycans by matrix-assisted laser desorption/ionization and electrospray ionization mass spectrometry", Proteomics, 2005, vol. 5, pp. 1774-1786.

Lattova, Erika et al., "Influence of the Labeling Group on Ionization and Fragmentation of Carbohydrates in Mass Spectrometry", Journal of the American Society for Mass Spectrometry, 2005, vol. 16, pp. 683-696.

Yamagaki, Tohru et al., "Semiquantitative analysis of isomeric oligosaccharides by negative-ion mode UV-MALDI TOF postsource decay mass spectrometry and their fragmentation mechanism study at N-acetyl hexosamine moiety", Journal of Mass Spectrometry, 2006, vol. 41, pp. 454-462.

International Search Report PCT/ISA/210, App. No. PCT/JP2006/306981, Jun. 13, 2006 (8 pages).

PCT/ISA/210 Corrected Version, (6 pages).

PCT/ISA/220 (1 page).

PCT/ISA/237 (7 pages).

Hiroaki Suzuki et al., "Fragmentation of Lewis type neutral-oligosaccharides in negative-ion MALDI-TOF mass spectrometry", The Chemical Society of Japan Dai 85 Shunki Nenkai Koen Yokoshu I, Mar. 11, 2005, p. 25.

Daisuke Sugahara et al., "Fluorescence Labeling of Oligosaccharides Useful in the Determination of Molecular Interactions", Analytical Sciences, Jan. 2003, pp. 167-169, vol. 19, The Japan Society for Analytical Chemistry, Japan.

Chris W. Brown et al., "Matrix Representations and Criteria for Selecting Analytical Wavelengths for Multicomponent Spectroscopic Analysis", Analytical Chemistry, 1982, vol. 54, pp. 1472-1479.

Y. Iida et al., Bunseki Kagaku, 1983, vol. 32, pp. 401-406.

Niclas G. Karlsson et al., "Negative ion graphitised carbon nano-liquid chromatography/mass spectrometry increases sensitivity for glycoprotein oligosaccharide analysis", Rapid Communications in Mass Spectrometry, 2004, 18: pp. 2282-2292.

Akihiko Kameyama et al., "Detection of Oligosaccharides Labeled with Cyanine Dyes Using Matrix-Assisted Laser Desorption/Ionization Mass Spectrometry", Analytical Chemistry, 2004, 76, pp. 4537-4542.

Communication from the Examining Division for the Patent No. EP1876441 (Application No. 06730929.4-1223) mailed Jun. 23, 2009.

Communication from the Examining Division for the Patent No. EP1876441 (Application No. 08730929.4-1223) mailed Nov. 16, 2009.

English Translation of International Preliminary Report on Patentability, for the Application No. PCT/JP2006/306981 mailed May 22, 2008.

* cited by examiner

METHOD OF NEGATIVE-ION MALDI ANALYSIS OF NEUTRAL LABELED SUGARS AND SCREENING DISEASE MARKERS

TECHNICAL FIELD

The present invention relates to a method for mass spectrometry of a sugar chain, and more specifically to a technique of elucidating structural information of a sugar chain which is essential for expression of function in a biological body by way of mass spectrometry. Further, the present invention relates to a method for screening disease marker and a method for analyzing a sample containing biomolecule, and more specifically, to a technique of elucidating structural information of a biomolecule which is essential for expression of function in a biological body by way of mass spectrometry and so on.

BACKGROUND ART

"Mass spectrometry" is a method which executes detection by ionizing a sample, and separating the ionized molecule according to mass/charge (m/z). Since acidic substances are likely to generate negative ions, and neutral substances are likely to generate positive ions, such ions are respectively measured.

Biopolymers such as nucleic acid, protein, sugar chain and the like are analyzed by conducting multi-stage MS measurement ($MS^n$ measurement). In multistage MS measurement, MS measurements are repeatedly conducted in such a manner that a parent ion which is generated at the first stage of MS measurement is chosen as a precursor ion and subjected to the second stage of MS measurement, and a precursor ion is chosen from product ions generated as a result and subjected to the third stage of MS measurement. This multistage MS measurement provides more specific structural information, however, it is necessary to generate abundant precursor ions to conduct the multistage MS measurement.

On the other hand, SUGAHARA, D et al., ANALYTICAL SCIENCE, 19, pp. 167-169 (2003) discloses that oligosaccharide is fluorescent-labeled and subjected to measurement by FP method or ELISA method.

Also, Brown, C. W, et al., Analytical Chemistry, Vol. 54, No. 9, pp. 1472 (1982), and Yasuo Iida et al., BUNSEKI KAGAKU, Vol. 32, pp. 401 (1983) disclose quantification methods regarding absorptiometry.

Further, on the other hand, Niclas G. Karlsson et al., Rapid Communications in Mass Spectrometry, 18, pp. 2282-2292 (2004) reports that structural specificity of $MS^2$ spectrum of neutral sugar is improved by LC-nano-ESI-MS (negative mode measurement).

DISCLOSURE OF THE INVENTION

Object of the Invention

In general, neutral molecules such as neutral sugar chains are stable when they are positive ions, and hence in MS/MS analysis, analysis is conducted while using $[M+Na]^+$ or $[M+H]^+$ as a precursor ion. However, for example when a fucose-containing sugar chain which attracts the attention as a disease marker is analyzed in positive mode, a number of ions in which fucose is dominantly lost generate. Among structural isomers having the same composition, product ions having the same composition (namely, having the same mass number) generate only with different ionic strengths, so that it is difficult to distinguish such product ions from one another. Therefore, it is impossible to conduct accurate identification of structure and screening of disease marker.

It is known that a negative ion is caused to generate from a non-labeled neutral sugar chain by electro-spray ionization (ESI) and the negative ion is measured by MS/MS. However, this is impracticable for diagnosis application because analysis is commonly complicated due to multivalent ions generated in ESI, and the sensitivity is low due to non-labeling.

In other attempts for negative ion measurement of non-labeled oligosaccharide having relatively simple structure by MALDI mass spectrometer, unconventional matrix such as norharman is used, or acidic substance such as HCl or $H_2SO_4$ is excessively added. However, satisfactory results are not obtained due to low sensitivity and overlapping with matrix peaks because $[M-H]^-$, $[M+Cl]^-$ or $[M+HSO_4]^-$ which is a parent ion is generated in a small amount, while partially fragmented ion species are abundantly generated.

It is an object of the present invention to provide a method for obtaining structural information conveniently and rapidly by generating a negative ion without adding an acidic substance to matrix, thereby improving sensitivity of measurement by a mass spectrometer, and by generating structural specific ions with high reproducibility.

It is another object of the present invention to provide a convenient and rapid screening method of disease marker and a method for analyzing a sample containing a biomolecule, by stably generating negative ions, thereby improving sensitivity of measurement by a mass spectrometer, and by generating structural specific ions with high reproducibility. It is also an object of the present invention to provide a method for diagnosing a particular disease using a disease marker.

SUMMARY OF THE INVENTION

The present inventors found that measurement sensitivity by mass spectrometer is improved by facilitating generation and stabilization of negative ion by labeling a sugar chain without adding an acidic substance to matrix. Further, the present inventors found that the negative ion thus generated allows generation of a structure specific ion with high reproducibility by $MS^n$ analysis, and accomplished a method for obtaining structural information conveniently and rapidly with high sensitivity.

The present invention includes the following inventive aspects <1> to <19>. The following inventive aspects <1> to <16> relate to a method for analyzing sugar chain.

<1> A method for mass spectrometry of a sugar chain comprising the steps of:
  preparing a sample containing a sugar chain;
  labeling the sugar chain with a labeling compound, to obtain a labeled sugar chain; and
  subjecting the labeled sugar chain to measurement of negative ions by using a MALDI mass spectrometer, thereby conducting analysis of the sugar chain.

<2> A method for mass spectrometry of a sugar chain comprising the steps of:
  preparing a sample containing sugar chains that are mutually structural isomers (A, B, C, . . . );
  labeling the sugar chains (A, B, C, . . . ) with a labeling compound, to obtain labeled sugar chains (A', B', C', . . . ); and
  subjecting the labeled sugar chains (A', B', C', . . . ) to measurement of negative ions by using a MALDI mass spectrometer to detect ions (a, b, c, . . . ) that specifically generate from the respective labeled sugar chains (A', B', C', ...), thereby distinguishing the sugar chains (A, B, C, ...) from one another.

Here, one kind or plural kinds of ion a, ion b, ion c, ... can be generated respectively from the corresponding labeled sugar chain.

<3> The method for mass spectrometry of a sugar chain according to <2>, wherein by conducting structure analysis for each of the ions (a, b, c, ...), an entire structure or a partial structure of the sugar chains (A, B, C, ...) is respectively identified.

<4> A method for mass spectrometry of a sugar chain comprising the steps of:
preparing a sample containing plural kinds of structural isomers of sugar chain in a known mixing ratio;
labeling the plural kinds of structural isomers of sugar chain with a labeling compound, to obtain a plural kinds of labeled structural isomers; and
subjecting the plural kinds of labeled structural isomers to measurement of negative ions by using a MALDI mass spectrometer to detect ions specifically generating from the respective plural kinds of labeled structural isomers, thereby analyzing the plural kinds of structural isomers of sugar chain.

<5> The method for mass spectrometry of a sugar chain according to <4>, wherein
by conducting structure analysis for the detected specifically generating ions, an entire structure or a partial structure of each of the plural kinds of structural isomers of sugar chain is identified, and/or
the detected specifically generating ions are determined as ions for quantification of the plural kinds of structural isomers, and relation between ion strength of the determined ion and the known mixing ratio is found.

<6> A method for mass spectrometry of a sugar chain comprising the steps of:
preparing a sample containing the plural kinds of structural isomers of sugar chain in an unknown mixing ratio;
labeling the plural kind of structural isomers with a labeling compound, to obtain a plural kinds of labeled structural isomers; and
subjecting the plural kinds of labeled structural isomers to measurement of negative ions by using a MALDI mass spectrometer to detect ions specifically generating from the respective plural kinds of labeled structural isomers, thereby analyzing the plural kinds of structural isomers of sugar chain,
wherein by conducting structure analysis for the detected specifically generating ions, an entire structure or a partial structure of each of the plural kinds of structural isomers of sugar chain is identified, and/or
from ion strength of detected specifically generating ion, the unknown mixing ratio is calculated based on the relation found in the method of <5>.

In the inventive aspects <1> to <6>, the sugar chain may have a known structure or an unknown structure. The following inventive aspects <7> to <9> show concrete aspects of structure identification methods in the case of sugar chain having an unknown structure.

<7> A method for mass spectrometry of a sugar chain comprising the steps of:
(1) preparing a sample containing one kind or plural kinds of sugar chain having an unknown structure;
labeling the sugar chain having the unknown structure with a labeling compound, to obtain a labeled sugar chain having the unknown structure;
subjecting the labeled sugar chain having the unknown structure to measurement of negative ions by using a MALDI mass spectrometer;
(2) separately, preparing a sample containing one kind or plural kinds of sugar chain having a known structure;
labeling the sugar chain having the known structure with the labeling compound, to obtain a labeled sugar chain having the known structure;
subjecting the labeled sugar chain having the known structure to measurement of negative ions by using a MALDI mass spectrometer; and
(3) comparing mass spectrum of the labeled sugar chain having the unknown structure obtained in (1) and/or information obtained from the mass spectrum, with mass spectrum of the labeled sugar chain having the known structure obtained in (2) and/or information obtained from the mass spectrum, to analyze the sugar chain having the unknown structure.

<8> The method for mass spectrometry of a sugar chain according to <7>, wherein in (3), it is ascertained that an entire mass spectrum peak of the labeled sugar chain having the unknown structure and/or an entire information obtained from the mass spectrum coincides with an entire mass spectrum peak of the labeled sugar chain having the known structure and/or an entire information obtained from the mass spectrum, thereby the sugar chain having the unknown structure is determined to have the same structure as the sugar chain having the known structure.

<9> The method for mass spectrometry of a sugar chain according to <7>, wherein in (3), it is ascertained that a particular peak in mass spectrum of the labeled sugar chain having the unknown structure and/or particular information obtained from the mass spectrum coincides with a particular peak in mass spectrum of the labeled sugar chain having the known structure and/or particular information obtained from the mass spectrum, thereby the sugar chain having the unknown structure is determined to have the same structure as the sugar chain having the known structure as a partial structure.

The following <10> to <13> are recitations about labeling compound.

<10> The method for mass spectrometry of a sugar chain according to any of <1> to <9>, wherein the labeling compound is a compound having a fundamental skeleton of aromatic.

<11> The method for mass spectrometry of a sugar chain according to <10>, wherein the aromatic is selected from the group consisting of pyrene, benzene and pyridine.

<12> The method for mass spectrometry of a sugar chain according to any of <1> to <11>, wherein the labeling compound is selected from the group consisting of aromatic amine and aromatic carboxylic acid hydrazide.

<13> The method for mass spectrometry of a sugar chain according to any of <1> to <12>, wherein the labeling compound is selected from the group consisting of pyrenebutanoic acid hydrazide, aminopyrene, 2-aminopyridine, 2-aminobenzene, amino benzoic acid, and amino benzoic acid ester.

The following <14> to <16> are recitations about sugar chain.

<14> The method for mass spectrometry of a sugar chain according to any of <1> to <13>, wherein the sugar chain is a sugar chain having fucose and/or sugar that is generated by subjecting acidic sugar to a neutralization process.

<15> The method for mass spectrometry of a sugar chain according to any of <1> to <13>, wherein the sugar chain is a sugar chain having fucose and/or acidic sugar, and the labeled sugar chain is obtained by conducting the labeling process and a neutralization process of the acidic sugar.

<16> The method for mass spectrometry of a sugar chain according to <14> or <15>, wherein the acidic sugar is selected from the group consisting of sialic acid, sulfate group containing sugar, and phosphate group containing sugar.

The inventive aspects of following <17> to <19> relate to data obtained by the methods of <1> to <16>.

<17> A mass spectrum obtained by:
labeling a sugar chain with a labeling compound to obtain a labeled sugar chain, and
subjecting the labeled sugar chain to measurement of negative ions by using a MALDI mass spectrometer.

<18> Information obtained from the mass spectrum according to <17>, containing information about ion species specifically generating from a particular structural isomer of sugar chain, and information about structural information of the particular structural isomer.

<19> Data set containing the mass spectrum according to <17> and/or the information according to <18>.

According to the inventive aspects described in <1> to <19>, it is possible to provide a method in which structural information is conveniently and rapidly obtained by labeling the sugar chain without adding an acidic substance to matrix to generate negative ions and improve sensitivity of measurement by mass spectrometer as well as generate structural specific ion with good reproducibility. Also according to the inventive aspects described in <1> to <19>, it is possible to provide a method which can be used advantageously in diagnosis of disease in which the sugar chain which can have structural isomers is involved.

Further, the present inventors found that it is possible to readily generate and stabilize a negative ion, and improve the sensitivity of measurement by a mass spectrometer by labeling a biomolecule. The inventors also found that such negative ion thus generated generates a structurally specific ion with high reproducibility by $MS^n$ analysis, and accomplished a method of sensitively, conveniently and rapidly screening disease marker and analyzing a sample containing biomolecule.

The present invention also includes the following inventive aspects <20> to <32>.

The following <20> to <27> relate to a screening method of disease marker.

<20> A method for screening disease marker, comprising the steps of:
(1) preparing a sample containing a biomolecule X derived from a subject affected by a particular disease;
labeling the biomolecule X with a labeling compound, to obtain a labeled biomolecule X';
subjecting the labeled biomolecule X' to measurement of negative ions by a MALDI mass spectrometer,
(2) separately, preparing a sample containing a biomolecule Y derived from a subject unaffected by the particular disease;
labeling the biomolecule Y with the labeling compound, to obtain a labeled biomolecule Y';
subjecting the labeled biomolecule Y' to measurement of negative ions by a MALDI mass spectrometer; and
(3) comparing mass spectrum of the labeled biomolecule X' obtained in (1) and/or information obtained from the mass spectrum, with mass spectrum of the labeled biomolecule Y' obtained in (2) and/or information obtained from the mass spectrum, to find mass spectrum peaks and/or information which are mutually different, thereby ascertaining presence of a structure involved in expression of the particular disease.

<21> The method for screening disease marker according to <20> comprising,
analyzing a structure involved in expression of the particular disease based on, among the found mass spectrum peaks or information which are different,
those having different mass/charge, included in mass spectrum of the labeled biomolecule X' and/or information obtained from the mass spectrum, but not included in mass spectrum of the labeled biomolecule Y' and/or information obtained from the mass spectrum, or
those having the same mass/charge and different in ion strengths, which are detected at stronger ion strength, in mass spectrum of the labeled biomolecule X' and/or information obtained from the mass spectrum, than in mass spectrum of the labeled biomolecule Y' and/or information obtained from the mass spectrum, and
determining the structure involved in expression of the particular disease or a structure of the biomolecule X as a structure of disease marker.

<22> The method for screening disease marker according to <20> or <21>, wherein the biomolecule is a sugar chain.

<23> The method for screening disease marker according to any of <20> to <22>, wherein the particular disease is cancer, and the biomolecule is sugar chain containing fucose and/or sialic acid, or blood group antigen.

<24> The method for screening disease marker according to any of <20> to <22>, wherein the particular disease is a disease caused by an autoimmune disease and having correlation with blood group, and the biomolecule is sugar chain containing fucose and/or sialic acid, or blood group antigen.

<25> The method for screening disease marker according to any of <20> to <22>, wherein the particular disease is heart disease or hypercholesterolemia, and the biomolecule is sugar chain containing fucose and/or sialic acid, or blood group antigen.

<26> The method for screening disease marker according to any of <20> to <25>, wherein the labeling compound is selected from the group consisting of pyrene derivatives, benzene derivatives and pyridine derivatives.

<27> The method for screening disease marker according to any of <20> to <26>, wherein the labeling compound is selected from the group consisting of pyrenebutanoic acid hydrazide, aminopyrene, 2-aminopyridine, 2-aminobenzene, amino benzoic acid, and amino benzoic acid ester.

The following <28> to <30> relate to a method for analyzing a sample containing a biomolecule.

Among these, <28> and <29> relate to a method for analyzing sample using mass spectrometry.

<28> A method for analyzing a sample containing a biomolecule, comprising the steps of:
preparing a sample containing a biomolecule Z derived from a subject;
labeling the biomolecule Z with a labeling compound, to obtain a labeled biomolecule Z';
subjecting the labeled biomolecule Z' to measurement of negative ions by a MALDI mass spectrometer; and
estimating presence/absence of expression of particular disease or level of the expression in the subject, based on obtained mass spectrum of the labeled biomolecule Z' and/or information obtained from the mass spectrum, while taking mass spectrum of disease marker and/or information obtained from the mass spectrum as an index.

<29> A method for analyzing a sample containing a biomolecule, comprising the steps of:
(1) preparing a sample containing a biomolecule Z derived from a subject;
labeling the biomolecule Z with a labeling compound, to obtain a labeled biomolecule Z';
subjecting the labeled biomolecule Z' to measurement of negative ions by a MALDI mass spectrometer;
(2) separately, preparing a disease marker;
labeling the disease marker with the labeling compound, to obtain a labeled disease marker;
subjecting the labeled biomolecule Z' to measurement of negative ions by a MALDI mass spectrometer;
(3) comparing mass spectrum of the labeled biomolecule Z' obtained in (1) and/or information obtained from the mass spectrum, with mass spectrum of the disease marker obtained in (2) and/or information obtained from the mass spectrum, to estimate presence/absence of expression of particular disease or level of the expression in the subject.

As the disease marker used in the methods of analyzing a sample containing a biomolecule according to <28> and <29>, a disease marker that is found in the method according to any of <20> to <27>, or a disease marker according to <31> or <32> below may be used.

<30> A method for analyzing a sample containing a biomolecule, comprising the steps of:
preparing a sample containing a biomolecule derived from a subject, and
estimating presence/absence of expression of particular disease or level of the expression in the subject by using a disease marker found in the method according to any of <20> to <27>.

As the disease marker in the method for analyzing a sample containing a biomolecule according to <30>, a disease marker described in <31> or <32> below may be used.

The following <31> and <32> relate to a disease marker.

<31> A disease marker found by the method according to any of <20> to <27>, having sugar chain structure containing fucose and/or sialic acid.

<32> A disease marker found by the method according to any of <20> to <27>, having sugar chain structure of blood group antigen.

The present invention also includes the following inventive aspects <33> to <35> relating to a diagnostic method of disease.

Among these, <33> and <34> relate to a method for diagnosing disease using mass spectrometry.

<33> A method for diagnosing disease, comprising the steps of:
preparing a sample containing a biomolecule Z derived from a subject;
labeling the biomolecule Z with a labeling compound, to obtain a labeled biomolecule Z';
subjecting the labeled biomolecule Z' to measurement of negative ions by a MALDI mass spectrometer; and
estimating presence/absence of expression of particular disease or level of the expression in the subject, based on obtained mass spectrum of the labeled biomolecule Z' and/or information obtained from the mass spectrum, while taking mass spectrum of disease marker and/or information obtained from the mass spectrum as an index, thereby diagnosing presence/absence of morbidity and degree of progression of the particular disease, and/or degree of therapeutic effect for the particular disease.

<34> A method for diagnosing disease, comprising the steps of:
(1) preparing a sample containing a biomolecule Z derived from a subject;
labeling the biomolecule Z with a labeling compound, to obtain a labeled biomolecule Z';
subjecting the labeled biomolecule Z' to measurement of negative ions by a MALDI mass spectrometer;
(2) separately, preparing a disease marker;
labeling the disease marker with the labeling compound, to obtain a labeled disease marker;
subjecting the labeled biomolecule Z' to measurement of negative ions by a MALDI mass spectrometer;
(3) comparing mass spectrum of the labeled biomolecule Z' obtained in (1) and/or information obtained from the mass spectrum, with mass spectrum of disease marker obtained in (2) and/or information obtained from the mass spectrum, to estimate presence/absence of expression of particular disease or level of the expression in the subject, thereby diagnosing presence/absence of morbidity and degree of progression of the particular disease, and/or degree of therapeutic effect for the particular disease.

As the disease marker used in the methods of diagnosing according to <33> and <34>, a disease marker that is found in the method according to any of <20> to <27>, or a disease marker according to <31> or <32> above may be used.

<35> A method for diagnosing disease, comprising the steps of: preparing a sample containing a biomolecule derived from a subject, and
estimating presence/absence of expression of particular disease or level of the expression in the subject by using a disease marker found in the method according to any of <20> to <27>, thereby diagnosing presence/absence of morbidity and degree of progression of the particular disease, and/or degree of therapeutic effect for the particular disease.

As the disease marker in the method for analyzing sample containing a biomolecule according to <35>, a disease marker described in <31> or <32> below may be used.

According to the inventive aspects described in <20> to <35>, it is possible to provide a method in which screening disease marker and analyzing sample containing biomolecule is conveniently and rapidly performed by labeling the biomolecule to facilely generate and stabilize negative ion and improve sensitivity of measurement by mass spectrometer as well as generate structural specific ion with good reproducibility. It is also possible to provide a method for diagnosing a particular disease using a disease marker obtained by the present invention.

MODES FOR CARRYING OUT THE INVENTION

Figure 1:
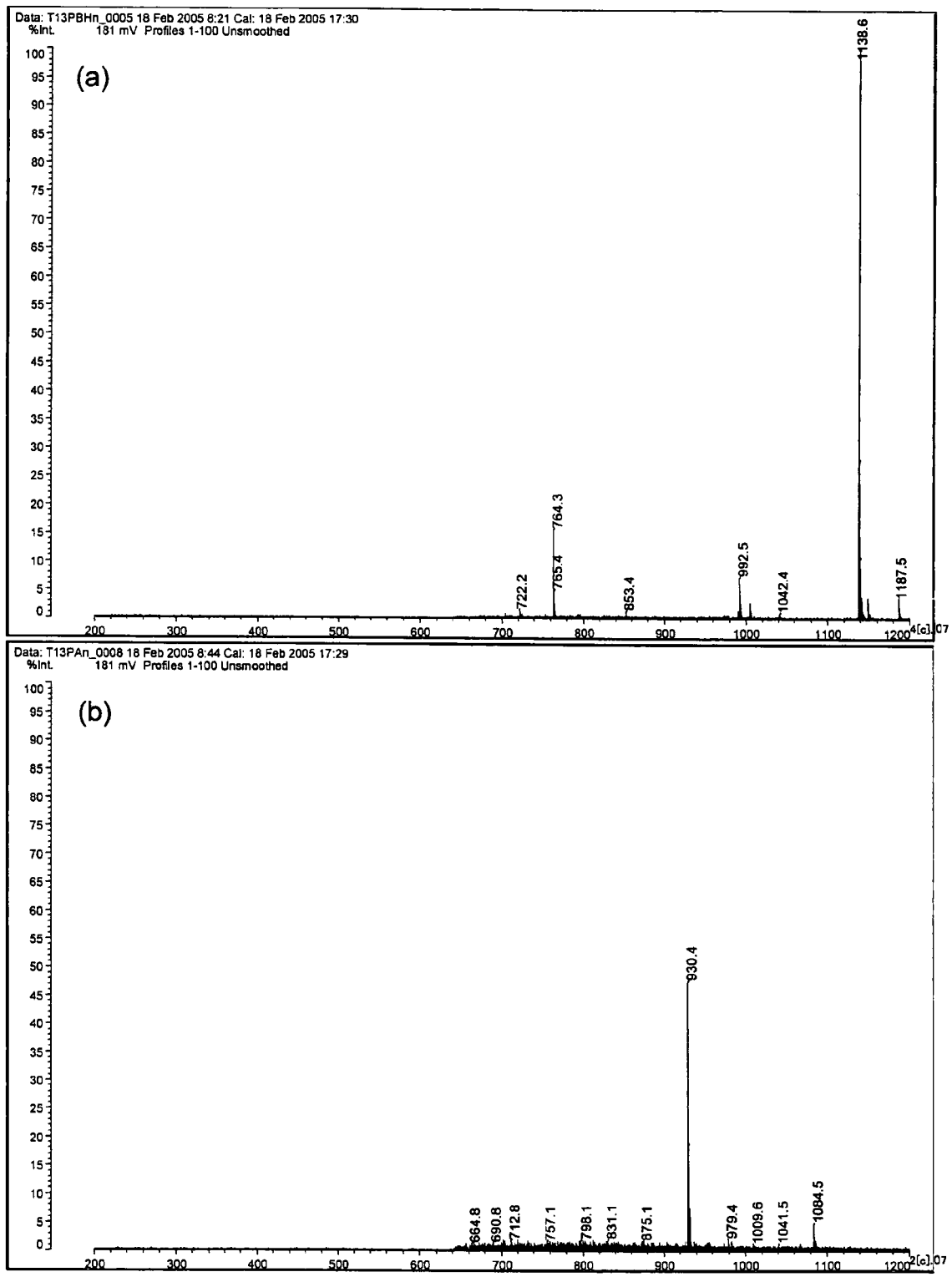
FIGS. 1 are (a) a negative ion MS spectrum of pyrene-labeled LNF-III, and (b) a negative ion MS spectrum of aminopyridine-labeled LNF-III.

[Method for Analyzing a Sugar Chain, and Data which can be Obtained Thereby]

First, explanation will be given for the above inventive aspects <1> to <19>.

The present invention comprises preparing a sample containing a sugar chain, labeling the sugar chain with a labeling compound, and subjecting the sugar chain to measurement of negative ions by mass spectrometry.

More specifically, the present invention comprises the following cases: the case including labeling a neutral sugar chain to obtain a labeled sugar chain, and subjecting the sugar chain to measurement of negative ions by a mass spectrometer; the case including preparing a neutral sugar chain obtained by subjecting an acidic sugar chain to neutralizing process, labeling the neutral sugar chain to obtain a labeled sugar chain, and subjecting the labeled sugar chain to measurement of negative ions; and the case including labeling an acidic sugar chain and then subjecting the an acidic sugar in the sugar chain to neutralizing process to obtain a labeled sugar chain, and subjecting the labeled sugar chain to measurement of negative ions.

In the following, the present invention will be described in detail.

<Preparation of Sample Containing a Sugar Chain>

In the present invention, the term "sugar chain" refers principally to sugar chains (oligosaccharides, polysaccharides), however it refers, for convenience, to general sugars also including monosaccharide. The term "neutral sugar chain" refers to a sugar chain having no charge.

Sugar chains in the present invention may be naturally occurring sugar chains or sugar chains prepared by chemical or enzymatic technique, and may have known or unknown structures. Therefore, Specific examples of the wordings "sample containing a sugar chain" include samples prepared from a fraction containing a sugar chain, obtained from living body-derived samples (for example, cells, tissues, secretions, bodily fluids and the like), and samples containing a specimen having known structure, obtained by chemical synthesis or enzymatic synthesis and the like.

Examples of sugar chains prepared by chemical or enzymatic techniques include those liberated from the glycoconjugate, those obtained by neutralizing acidic sugar chain, and the like.

Examples of the glycoconjugate include glycoprotein and glycolipid and the like. When the sample to be subjected to mass spectrometry contains such glycoconjugate, a sample of the present invention is prepared by preliminarily conducting a process for liberating a sugar chain moiety from the glycoconjugate by a chemical or enzymatic technique.

When the sample to be subjected to mass spectrometry contains an acidic sugar chain, e.g. in the case where an acidic sugar chain is generated by a process of liberating the sugar chain as described above or the like cases, a neutralization process is made on the acidic sugar residue in the sugar chain. Neutralization process of acidic sugar residue may be carried out in the stage before labeling, or in the stage after labeling and before mass spectrometry. Examples of the acidic sugar chain include those containing acidic sugar such as sialic acid, sulfuric acid group containing sugar, phosphoric acid group containing sugar or the like as a constituting sugar. As a method of neutralization of acidic sugar chain, methods in which modification of liberation of sialic acid, sulfuric acid group, phosphoric acid group and the like are chemically or enzymatically conducted, or the like methods are exemplified.

Specific examples of a sugar chain to be analyzed include core structure of N-liked sugar chain bonded to Asn (high mannose type, hybrid type, complex type), core structure of O-liked sugar chain bonded to Thr/Ser, and sugar chains in which a sugar chain is further extended in linear form or branched from the above core structures.

The sugar chain having biological activity has as a side chain moiety extended from the above core structure, Galβ1-3GlcNAc, Galβ1-4GlcNAc, GlcNAcβ1-6(GlcNAcβ1-3)Gal, GalNAcβ1-4Gal, GlcNAcα1-4Gal, GalNAcβ1-4GlcNAc, Galα1-3Gal, GalNAcα1-3Gal, Fucα1-2Gal, Fucα1-3GlcNAc, Fucα1-4GlcNAc, Fucα1-6GlcNAc and the like sugar chain or combination of sugar chains as described above.

Especially, in a practical example of the present invention, a sugar chain involved in a particular disease is an object to be analyzed.

As a sugar chain involved in a particular disease, sugar chains containing fucose, sugar chains containing fucose and/or the above acidic sugar (particularly sialic acid) and the like may be exemplified. Sugar chains containing fucose are directly subjected to the steps of labeling and mass spectrometry of the present invention. The sugar chain containing acidic sugar is, as described above, subjected to neutralization process prior to the labeling and then the steps of labeling and mass spectrometry of the present invention, or subjected to labeling followed by neutralization of acidic sugar residue, and then the step of mass spectrometry.

Specific examples of a sugar chain involved in a particular disease include ABO blood group antigens and Lewis blood group antigens. Examples of Lewis blood group antigens have sialic acid. These sugar antigens are involved in various biological activities and diseases. These sugar chains (sugar chains containing fucose and/or sialic acid, or blood group antigen sugar chains) express not only on the surface of blood cell, but also on sugar chains, glycolipids, glycoproteins and the like in epithelial tissues and secretory fluids and have important relationships with inflammatory diseases, autoimmune diseases, allergenic diseases, viral diseases, cancerous diseases, infectious disease, heart disease, hypercholesterolemia and the like.

For example, correlation with blood group is reported in infections of cholera vibrio, Salmonella, Helicobacter pylori, Campylobacter, influenza virus, Norwalk virus, rhino virus, eco virus and the like. Direct interaction have been ascertained between various pathogenic microorganisms including the examples as recited herein and sugar chains containing fucose and/or sialic acid and blood group antigen sugar chains.

In colon cancer, stomach cancer, bladder cancer, lung cancer, breast cancer, hepatic cancer, pancreas cancer and the like cancers, changes in expression of antigens containing fucose and/or sialic acid and blood group antigens are recognized. Such change in expression occurs from precancerous state, and is closely related with progression of disease and therapy for disease, and has high correlation with disease condition.

Further, the risk of heart disease is also correlated with blood group. This is attributable to the fact that blood cholesterol, LDL level, and blood pressure are correlated with blood group, and activity of blood-clotting factor is influenced by blood group antigen.

Moreover, examples of disease in which a particular disease is caused by autoimmune disease, and is correlated with blood group include pediatric steatosis, non-insulin-dependent diabetes, Grave's disease, ankylosing spondilitis and the like.

As the sugar chain which involved in a particular disease but has no fucose, GalNAcβ1-4GlcNAc may be exemplified. This sugar chain is found in pituitary hormone, and it has been reported that this sugar chain plays a role of controlling blood clearance, and abundance of this structure is reduced in the case of blast cancer. On the other hand, a sugar chain containing GlcNAcα1-4Gal is proved to have an activity of inhibiting proliferation of Helicobacter pylori.

Besides the above, it is proved that various antigens containing fucose and/or sialic acid are expressed in particular stages of generation and differentiation, and it seems to be important for expression of cellular function.

<Labeling of a Sugar Chain Using Labeling Compound>

In the present invention, the term "labeling compound" refers to a compound that is able to generate a negative ion from sugar chain in mass spectrometry by binding to the sugar chain. A labeling compound has a reactive group capable of covalently bonding with sugar chain, and a molecular skeleton capable of absorbing or emitting light.

More specifically, a compound having an aromatic fundamental skeleton may be exemplified as a labeling compound. Examples of the aromatic fundamental skeleton include, but are not limited to, pyrene, benzene, pyridine, and the like. More specifically, aromatic amines, aromatic carboxylic acid hydrazides and the like aromatic compound derivatives may be exemplified as a labeling compound. For example, pyrenebutanoic acid hydrazide (PBH), aminopyrene, 2-aminopyridine, 2-aminobenzene, amino benzoic acid, and esters of amino benzoic acid and the like may be exemplified. Among these labeling compounds, in the present invention, 2-aminopyridine or PBH is preferably used, and PBH is most preferably used.

The method of labeling is not particularly limited, and for example, labeling method that is conventionally employed, such as pyridyl-amination method and the like may be employed or appropriately applied.

For example, among the labeling compounds exemplified in the above, the compounds other than PBH may be used in such a manner that a labeling compound is reacted with a dried solid sugar chain in the presence of acid, and then reduced with the use of a reducing agent. Conditions of reagent, solvent, reaction temperature, reaction time and the like are not particularly limited, and may be determined appropriately by those skilled in the art. Therefore, examples of reaction conditions may be: hydrochloric acid or acetic acid and the like as the above acid; NaBH$_3$CN, NaBH$_4$ and the like as the reducing agent; methanol and the like as the solvent; about 80 to 90° C. as the reaction temperature; and as the reaction time, about 10 to 60 minutes for reaction between sugar chain and labeling compound, and about 10 to 60 minutes for reduction reaction. Conducting reduction in such a manner is desired from the view point of sensitivity of multistage MS measurement because it will stabilize the label of the sugar chain, and cause increase in ion strength of parent ion in the mass spectrometry as will be described later.

The above reducing agent is not necessarily required when PBH is used among the labeling compounds exemplified in the above.

When reduction is not used, a labeling compound may be reacted with a dried solid sugar chain in the presence of acid, and then neutralization may be conducted, and a labeled sugar chain may be extracted. One specific exemplary method in such a case is described in D. SUGAHARA, J. AMANO, and T. IRIMURA, ANALYTICAL SCIENCE, 19, 167-169 (2003).

When a reducing agent is used, a reducing agent solution may be added after carrying out the above neutralization, and reaction may be allowed at temperature between room temperature and 40° C. for about 10 to 60 minutes. In this case, it is more preferred to newly add a reducing agent solution and conduct reaction in the same manner.

In the manner as described above, a labeled sugar chain is obtained.

<Mass Spectrometric Measurement and Sugar Chain Analysis>

The obtained labeled sugar chain is measured in negative mode by a matrix-assisted laser desorption/ionization (MALDI) mass spectrometer.

As the matrix, α-cyano-4-hydroxycinnamic acid, norharman, 2,5-dihydroxy benzoic acid (DHBA) or the like is used.

In the present invention, preferably DHBA is used as the matrix, and measurement is conducted using a MALDJ-QIT-TOF mass spectrometer in which quadruple ion trap (QIT) and time-of-flight (TOF) are combined.

As a measurement method using a mass spectrometer, PSD measurement, ISD measurement, MS$^n$ measurement (multistage MS measurement; including tandem mass measurement) or the like method is used.

In the present specification, the first measurement executed by the mass spectrometer is referred to as MS measurement, and a particular ion (molecular weight-related ion and the like) is selected from ion peaks of the spectrum obtained in the MS measurement, and the second measurement using the selected particular ion as a precursor ion is referred to as MS$^2$ measurement (MS/MS measurement), and analysis by conducting MS$^2$ measurement (MS/MS measurement) is referred to as MS$^2$ analysis (MS/MS analysis; tandem mass analysis). Likewise the above, a particular ion is selected from ion peaks of the spectrum obtained in the MS$^{n-1}$ measurement, and the n-th measurement using the selected particular ion as a precursor ion is referred to as MS$^n$ measurement, and analysis by conducting MS$^n$ measurement is referred to as MS$^n$ analysis.

Analysis of sugar chain is conducted on the basis of mass number and relative strength of negative ion in measured mass spectrum. In the present invention, analysis of sugar chain includes structural analysis and quantitative analysis. Structural analysis includes assignment of detected ion species; detection and assignment of ion species which is specifically generated from a particular structural isomer of sugar chain (discrimination of structural isomers); identification of binding position of particular sugar; identification of partial structure of sugar chain; identification of entire structure of sugar chain and the like. Quantitative analysis includes detection of ion species capable of quantifying a particular sugar chain or ion species which is specifically generated from a particular structural isomer of sugar chain, and derivation of relation between ion strength of the ion species and relative amount in the sample; and quantification of a particular sugar chain or a particular structural isomer of sugar chain.

Sugar chain may have a plurality of structural isomers having the same molecular weight and the same monosaccharide composition. The aforementioned sugar chains that are related to particular diseases are also sugar chains in which structural isomers may exist. For example, when one fucose is bound to a sugar chain, there are possibly at least four binding formats (i.e., 1-2, 1-3, 1-4 and 1-6 glucoside bond) for each binding position of the one fucose (that is, position of sugar residue at which fucose binds in the sugar chain). Considering combination between binding format and binding position, significant number of structural isomers are expected as candidates. If the number of binding fucose is two, the number of such combination will further increase.

The present invention is particularly advantageously used when the sugar chain can have such structural isomers. When a plurality of structural isomers are to be analyzed in the present invention, each of the structural isomers may be contained in different independent samples, or a plurality of structural isomers may be contained in the same sample. In any cases, it is possible to distinguish the structural isomers from each other and to analyze the structural isomers thereof as will be described later.

For example, as the sugar chain, when sugar chains which have a relation of mutual structural isomers (A, B, C, . . . ) are to be analyzed, structural analysis may be conducted in the following manner.

In a same manner as described above, by labeling with the use of the aforementioned labeling compound, labeled sugar chains (A', B', C', . . . ) are obtained respectively from the sugar chains (A, B, C, . . . ).

Negative ions are measured by a mass spectrometer in a same manner as described above.

By conducting MS measurement of negative ions, molecular ions having the same (m/z) value are generated from the respective structural isomers. Taking the molecular ion as a precursor ion, MS/MS (or multistage MS of $MS^3$ or more) measurement is conducted, and specific ions (a, b, c, . . . ) which are specific to the respective structural isomers are detected. Here, one or more than one kind of specific ions may be generated from one kind of structural isomer. That is, product ion is specifically generated from each of the labeled sugar chains, in such a manner that from labeled sugar chain A', one kind or plural kinds of product ion a is generated, and from labeled sugar chain B', one kind or plural kinds of product ion b is generated, and from labeled sugar chain C', one kind or plural kinds of product ion c is generated.

By detecting such product ion, it is possible to distinguish structural isomers (A, B, C, . . . ) from each other.

More specifically, when two kinds of sugar chains, sugar chain A and sugar chain B which are in relation of mutual structural isomers are analyzed as the sugar chains, structural analysis may be conducted in the following manner.

In a same manner as described above, by labeling with the use of the aforementioned labeling compound, labeled sugar chain A' is obtained from sugar chain A, and labeled sugar chain B' is obtained from sugar chain B.

Negative ions are measured by a mass spectrometer in a same manner as described above.

By conducting MS measurement of negative ions, molecular ions having the same (m/z) value are generated from the respective structural isomers. Taking this molecular ion as a precursor ion, MS/MS (or multistage MS of $MS^3$ or more) measurement is conducted, and a specific ion is detected for each of the structural isomers. Assuming that one kind or plural kinds of product ion a is generated from labeled sugar chain A', and one kind plural kinds of product ion b is generated from labeled sugar chain B', relation between product ions a and b is as follows. That is, from labeled sugar chain A', at least one of product ions b is not generated, and from labeled sugar chain B' at least one of product ions a is not generated; and also, combination of mass number differs between product ions a and product ions b. In this manner, negative ion is generated in reflection of very small difference in structure. Therefore, it becomes possible to readily distinguish structural isomers from each other which was impossible in conventional mass spectrometry.

When $MS^n$ analysis is used in the present invention, this specific ion may usually be detected by $MS^2$ analysis, however, a new specific ion can be detected by conducting $MS^3$ analysis or further $MS^n$ analysis depending on the particular case. Detecting more specific ions in this manner is also desirable to obtain more specific information.

It is also possible to distinguish structural isomers, and identify partial or entire structure of structural isomer from information of detected ion. In particular, analyzing an ion specifically generated from a structural isomer may contribute to determination of important partial structure such as a minimum structure of a structure which is a determinant group of antigen or of a structure which is a key for expression of function in sugar chain. Of course, entire structure of structural isomer can be identified not only by analyzing such specific ion, but also by analyzing the ion that is commonly detected in structural isomers.

In the following, detailed explanation will be given for the case where a plural kinds of sugar chains are contained in a sample.

It is often the case that a biological sample is a mixture of various kinds of sugar chains. When the plural sugar chains contained in a sample are sugar chains mutually having different molecular weights, analysis can be readily conducted. For example, considering the case where a plural kinds of fucose containing sugar chains are contained in a sample, one sugar chain having one residue of fucose bound thereto while another sugar chain having two residues of fucose bound thereto. Such sugar chains mutually having different fucose binding numbers can be readily distinguished, identified and quantified by mass spectrometry because molecular weights are mutually different.

However, as previously described, a sugar chain can include a plurality of structural isomers having the same molecular weight and the same monosaccharide composition. The present invention is advantageously used when plural kinds of sugar chains contained in a sample are in relation of mutual structural isomers. In the method of the present invention, presence of other molecule in a sample on measurement will not influence on the phenomenon in which a particular product ion is specifically generated from a particular structural isomer. That is, ionization occurs dependently and specifically for individual structural isomer. Therefore, also in this case, analysis may be conducted according to the method as described above. That is, by detecting a product ion that is specifically generated from a particular structural isomer, quantification as well as identification of structural isomer is enabled.

For example, analysis may be conducted in the following manner. In the example of analysis method described below, description is given for quantification method, however, entire structure or partial structure of sugar chain can be identified by principally using information of product ion generated specifically from a particular structural isomer, as described above.

A sample containing plural kinds of structural isomers of sugar chain in known mixing ratio is prepared.

In the same manner as described above, plural kinds of sugar chains are labeled with the use of the aforementioned labeling compound to give a plural kinds of labeled structural isomers.

In the same manner as described above, negative ions are measured by a mass spectrometer.

A specific ion is detected for each of the plural kinds of labeled structural isomers by mass spectrometric measurement. By the specific ion obtained according to the present invention for the structural isomers, the plural kinds of structural isomers can be distinguished.

As described above, when $MS^n$ analysis is used in the present invention, the specific ion can usually be detected by $MS^2$ analysis, however, it is also preferred to detect more specific ions by conducting $MS^3$ analysis or further $MS^n$ analysis depending on the particular case, thereby obtaining more detailed information.

As described above, in the present invention, presence of other molecule in a sample on measurement will not influence on the phenomenon in which a particular product ion is specifically generated from a particular structural isomer. Therefore, detected specific ions are detected in ion strength ratio reflecting mixing ratio of the structural isomers contained in the sample. Based on this fact, an ion specifically generated from a structural isomer may be used as an ion for quantification of the structural isomer.

Therefore, in the quantification analysis, specifically, an ion specifically generated from a structural isomer is determined as an ion for quantification of the structural isomer, and it is possible to find relation between ion strength of ion for quantification and known mixing ratio based on the known mixing ratio of plural structural isomers contained in the sample. For example, when structural isomers X and structural isomers Y are contained in the sample in a ratio which is the same with the above known mixing ratio, the strength ratio between particular ion x generated from structural isomer X and particular ion y generated from structural isomers Y is always identical; and such relation can be found that when an amount of structural isomers X relative to structural isomers Y in the sample changes, ion strength of ion x relative to ion y will change in multiple proportion to relative mixing amount.

As described above, information of the ion for quantification that is obtained by determining the ion and finding relation between the ion strength and a present ratio of structural isomer in the sample may be advantageously used in quantitative analysis in the case where a plurality of structural isomers are present in the sample in unknown mixing ratio. For example, the unknown mixing ratio may be calculated in the following manner.

A sample containing plural kinds of structural isomers of sugar chain in unknown mixing ratio is prepared.

In the same manner as described above, a plurality of structural isomers are labeled with a labeling compound to give plural kinds of labeled structural isomers.

In the same manner as described above, negative ions are measured by a mass spectrometer.

A specific ion is detected for each of the plural kinds of labeled structural isomers. Comparison is made for a set of ions having the same mass number, an ion detected in the above and an ion for quantification, and unknown mixing ratio is calculated from ion strength of the detected ion, based on the relation between ion strength of ion for quantification and mixing ratio in the sample, found in the aforementioned manner. In the manner as described above, quantification may be made for a plurality of structural isomers of sugar chain.

Identification of structure of sugar chain having the unknown structure in the present invention may be achieved, for example, by obtaining a mass spectrometry result of the sugar chain having the unknown structure according to the method of the present invention and comparing the mass spectrometry result with a mass spectrometry result of sugar chain having known structure. The followings are exemplary embodiments for carrying out identification of structure in this manner, however, the embodiments given herein also include the cases where plural kinds of structural isomers of sugar chain are analyzed as described above.

(1) Prepare a sample containing a sugar chain having the unknown structure.

Label the sugar chain having the unknown structure with a labeling compound, to give labeled sugar chain having the unknown structure.

Measure the labeled sugar chain having the unknown structure in negative mode by using a MALDI mass spectrometer.

(2) Separately, prepare a sample containing a sugar chain having known structure.

Label the sugar chain having known structure with a labeling compound, to give labeled sugar chain having known structure.

Measure the labeled sugar chain having known structure in negative mode by using a MALDI mass spectrometer.

(3) Compare mass spectrum of the labeled sugar chain having the unknown structure obtained in (1) and/or information obtained from the mass spectrum, with mass spectrum of the labeled sugar chain having known structure obtained in (2) and/or information obtained from the mass spectrum.

Here, information obtained from mass spectrum includes structural information of product ion itself, position on the precursor ion where fragmentation that generates its product ion occurred, putative information about liberated neutral molecule, and information derived from combination of these information.

In the above step (3), the sugar chain having the unknown structure may be determined to have the same structure as the sugar chain having known structure, if it is determined that entire peak in mass spectrum of the labeled sugar chain having the unknown structure and/or entire information obtained from the mass spectrum coincides with entire peak in mass spectrum of the labeled sugar chain having known structure and/or entire information obtained from the mass spectrum.

When the expression "entire mass spectrum" is used, the peak to be compared should contain at least a major peak (namely, a peak detected in a certain degree of ion strength) and/or a peak which is essential for analyzing the entire structure of sugar chain. When the expression "entire information obtained from mass spectrum" is used, the information to be compared should contain at least information essential for the entire structure of sugar chain.

The term "coincide" or "coincidence" allows error within the measurement range of mass spectrometer when mass number or ion strength of generated ion is compared. Further, when information about structure such as sugar chain sequence or position on sugar chain is compared, perfect coincidence is required.

In the above method, structure of entire sugar chain can be determined. However, a sugar chain having the unknown structure takes an extremely various kind of structures, while the number of kinds of sugar chain having known structure which is available as a standard is limited. It is sometimes the case that determination of only a minimum structure such as structure that is a determinant for antigen or structure that is a key for expression of function in the sugar chain suffices rather than clarifying the entire structure of the sugar chain. Determining such partial structure is important. In the present invention, partial structure may be determined in the following manner.

That is, in the above step (3), if it is determined that a particular peak in mass spectrum of the labeled sugar chain having the unknown structure and/or a particular information obtained from the mass spectrum coincides with a particular peak in mass spectrum of the labeled sugar chain having known structure and/or a particular information obtained from the mass spectrum, the sugar chain having the unknown structure may be determined to have the same structure as the sugar chain having known structure in the particular part.

For example, in the above step (3), if it is determined that a partial peak in mass spectrum of the labeled sugar chain having the unknown structure and/or a partial information obtained from the mass spectrum coincides with an entire peak in mass spectrum of the labeled sugar chain having known structure and/or an entire information obtained from the mass spectrum, the sugar chain having the unknown structure may be determined to have the same structure as the sugar chain having known structure as its partial structure.

In the following, description will be given about data obtained by the method of the present invention.

From the mass spectrum obtained by the method of the present invention (namely, the mass spectrum obtained by labeling a sugar chain, and subjecting the obtained labeled sugar chain to measurement of negative ions by a MALD mass spectrometer), important information about the sugar chain is obtained. For example, structural information of product ion including product ion specifically generated from a structural isomer, position on the precursor ion where fragmentation that generates the product ion occurred, putative information about liberated neutral molecule, and structural information or quantitative information derived from combination of these information may be exemplified. A mass spectrum containing such important information can be utilized as data concerning sugar chain.

For example, with respect to a variety of sugar chains having known structures, a variety of mass spectrums are obtained using the method of the present invention, and the obtained mass spectrums and/or information obtained from the mass spectrums may be stored as data sets. Further, such data sets may contain mass spectrums of those having structure that is proved by the method of the present invention and/or information obtainable from such mass spectrums.

Data contained in such data sets may be used as structural data of sugar chain having known structure for comparison when a mass spectrometry result of a sugar chain having the unknown structure is compared with a mass spectrometry result of sugar chain having known structure to thereby determine the unknown structure in the manner as described above.

In the following, an effect of the present invention will be described.

First, since stable generation of negative ion is enabled in mass spectrometry, it becomes possible to generate a sufficient amount of precursor ions for enabling multistage MS measurement, and to realize mass spectrometry with high sensitivity. Further, in a negative ion of labeled sugar chain, α-glycoside bond of fucose or sialic acid after neutralization is stable, so that information about bonding position of these can be obtained from the fact that generation amount of product ions from which such sugar chain is eliminated is relatively reduced.

Further, since negative ions of labeled sugar chain are generated in reflection of very small structure, they exhibit effectiveness in distinguishing complicated and wide variety of structural isomers. Capability of distinguishing structural isomers is equivalent to ability to obtain important information telling attachment to a particular position in sugar chain via a particular bond.

Therefore, the method of the present invention may be used for diagnosis of various diseases by being applied to sugar chains that are involved in particular diseases as described in the present specification. For example, in analysis of a fucose containing sugar chain by the method of the present invention, revealing the binding position of fucose will be sufficiently advantageously used for diagnosis of disease in which the fucose containing sugar chain is involved. Further, since it is clarify whether a particular fucose bond is contained in a sugar chain having the unknown structure based on information obtained from fucose-containing sugar chain having known structure, the method can be used as a new and convenient diagnostic method.

It is further notable that by applying the present invention, it becomes possible to identify and quantify structural isomers by detecting a structure specific ion even when plural kinds of structural isomers of sugar chain are contained in a sample. Requested in diagnosis of disease is to clarify which structural isomer is present in what amount rather than clarifying presence or absence of structural isomers, however, conventionally, operation of separating sugar isomers is very complicated and requires specialized technique. In diagnosis using a very small amount of biological sample, in particular, complicated and time-consuming separating operation is inappropriate. Therefore, the method of the present invention enables identification and quantification at high sensitivity even when the structural isomers are in mixture, so that it has high practicability to diagnosis of disease.

[Method for Screening Disease Marker, Disease Marker Found by the Method, Method for Analyzing Biological Sample, and Method for Diagnosing Disease]

Next, inventive aspects described in the above <20> to <35> will be explained below.

The present invention includes the following basic steps: preparing a sample containing a biomolecule, labeling the biomolecule with a labeling compound, and subjecting the obtained labeled biomolecule to measurement of negative ions by mass spectrometry. For example, when the biomolecule is a sugar chain, a sample containing sugar chain is prepared, the sugar chain is labeled with a labeling compound, and subjecting the labeled sugar chain to measurement of negative ions by mass spectrometry. More specifically, the following cases are included: the case including labeling a neutral sugar chain to obtain a labeled sugar chain, and subjecting the labeled sugar chain to measurement of negative ions by mass spectrometer; the case including preparing a neutral sugar chain obtained by subjecting an acidic sugar chain to neutralization process, labeling the neutral sugar chain to obtain a labeled sugar chain, and subjecting the labeled sugar chain to measurement of negative ions of the labeled sugar chain; and the case including labeling an acidic sugar chain and subjecting an acidic sugar in the sugar chain to neutralization process to obtain a labeled sugar chain, and subjecting the labeled sugar chain to measurement of negative ions.

The method for screening disease marker and the method for mass spectrometry of a sample containing biomolecule of the present invention are conducted by applying the above basic steps.

First, in the following the basic steps of the present invention will be described in detail.

<Preparation of Sample Containing Biomolecule>

In the present invention, the term "biomolecule" refers to sugar chains, proteins and peptides, or proteins and peptides modified with sugar chain and the like, nucleic acids, glycolipids and the like. These biomolecules may be naturally occurring biomolecules or biomolecules prepared by chemical or enzymatically technique, and may have known or the unknown structures. Therefore, Specific examples of the wordings "sample containing a biomolecule" include fraction samples containing a biomolecule, prepared from living body-derived samples (for example, cells, tissues, secretions, bodily fluids), and samples containing a specimen having known structure, obtained by chemical synthesis or enzymatic synthesis and the like.

These biomolecules properly function while their expression level is controlled depending on the time and occasion. Functional failure could occur only when a part of structure of the molecule is deficient or changed.

Therefore, clarification of structural change of such biomolecule will make prophylaxis, diagnosis and therapy of disease possible. In glycoprotein, in particular, it is reported that a sugar chain structure in disease condition is different although the same peptide chain as that in healthy condition is possessed. It is also reported that change in sugar chain are different depending on the degree of progression of clinical condition, whether the disease is acute or chronic, whether the disease is benign or malignant, or therapeutic process for the disease. Therefore, by taking changes in sugar chain structure into account as well as presence/absence of expression of protein, more accurate information of clinical condition can be obtained.

For example, when the biomolecule is a sugar chain, a sample containing biomolecule may be prepared in the manner as described in <Preparation of sample containing sugar chain> in [Method for analyzing sugar chain, and data obtainable by the method] describing the above inventive aspects <1> to <19>.

<Labeling of Biomolecule Using Labeling Compound>

In the present invention, the term "labeling compound" refers to a compound that is able to generate a negative ion from biomolecule in mass spectrometry by binding to the biomolecule. A labeling compound has a reactive group capable of covalently bonding with biomolecule, and a molecular skeleton capable of absorbing or emitting light.

The method of labeling is not particularly limited, and a labeled biomolecule may be obtained by appropriately using techniques that are conventionally conducted.

For example, when the biomolecule is a sugar chain, the labeling compound and the labeling method are as described in <Labeling of sugar chain using labeling compound> in [Method for analyzing sugar chain, and data obtainable by the method] describing the above inventive aspects <1> to <19>.

<Mass Spectrometric Measurement and Analysis of Biomolecule>

The obtained labeled biomolecule is measured in negative mode by a matrix-assisted laser desorption/ionization (MALDI) mass spectrometer.

As the matrix, α-cyano-4-hydroxycinnamic acid, norharman 2,5-dihydroxy benzoic acid (DHBA) or the like is used.

In the present invention, preferably DHBA is used as the matrix, and measurement is conducted using a MALDI-QIT-TOF mass spectrometer in which quadruple on trap (QIT) and time-of-flight (TOF) are combined.

As a measurement method using a mass spectrometer, PSD measurement, ISD measurement, $MS^n$ measurement (multi-stage MS measurement; including tandem mass measurement) or the like method is used.

Analysis of biomolecule is executed based on mass number and relative strength of negative ions in measured mass spectrum. In the present basic steps, analysis of biomolecule includes structural analysis and quantitative analysis. By conducting structural analysis, it is possible to know, for example, the structure of biomolecule involved in a particular disease, so that screening of disease marker is enabled. Further, by conducting quantitative analysis, it is possible to know, for example, the present amount of biomolecule involved in a particular disease, so that presence/absence of expression of particular disease or degree of expression, that is, presence/absence, progression stage, degree of therapeutic effect for a particular disease can be diagnosed.

For example in the case of sugar chain as a biomolecule, more specifically, structural analysis includes assignment of detected ion species; detection and assignment of ion species which is specifically generated from a particular structural isomer of sugar chain (discrimination of structural isomers); identification of binding position of particular sugar; identification of partial structure of sugar chain; identification of entire structure of sugar chain and the like. Quantitative analysis includes detection of ion species capable of quantifying a particular sugar chain or ion species which is specifically generated from a particular structural isomer of sugar chain, and derivation of relation between ion strength of the ion species and relative amount in the sample; and quantification of a particular sugar chain or a particular structural isomer of sugar chain.

In the following, the method for analyzing biomolecule will be explained with showing the case that the biomolecule is sugar chain as an example. Regarding the other biomolecules, the structural analysis and the quantitative analysis are enabled likewise in the following method for analyzing sugar chain.

Sugar chain may have a plurality of structural isomers having the same molecular weight and the same monosaccharide composition. The aforementioned sugar chains that are related to particular diseases are also sugar chains in which structural isomers may exist. For example, when one fucose is bound to a sugar chain, there are possibly at least four binding formats (i.e., 1-2, 1-3, 1-4 and 1-6 glucoside bond) for each binding position of the one fucose (that is, position of sugar residue at which fucose binds in the sugar chain). Considering combination between binding format and binding position, significant number of structural isomers are expected as candidates. If the number of binding fucose is two, the number of such combination will further increase.

The present basic step is particularly advantageously used when the sugar chain can have such structural isomers. When a plurality of structural isomers are to be analyzed in the present basic step, each of the structural isomers may be contained in different independent samples, or a plurality of structural isomers may be contained in the same sample. In any cases, it is possible to distinguish the structural isomers from each other and to analyze the structural isomers thereof as will be described later.

For example, as the sugar chain, when sugar chains which have a relation of mutual structural isomers (A, B, C, . . . ) are to be analyzed, structural analysis may be conducted in the following manner.

In a same manner as described above, by labeling with the use of the aforementioned labeling compound, labeled sugar chains (A', B', C', . . . ) are obtained respectively from the sugar chains (A, B, C, . . . ).

Negative ions are measured by a mass spectrometer in a same manner as described above.

By conducting MS measurement of negative ions, molecular ions having the same (m/z) value are generated from the respective structural isomers. Taking the molecular ion as a precursor ion, MS/MS (or multistage MS of $MS^3$ or more) measurement is conducted, and specific ions (a, b, c, . . . ) which are specific to the respective structural isomers are detected. Here, one or more than one kind of specific ions may be generated from one kind of structural isomer. That is, product ion is specifically generated from each of the labeled sugar chains, in such a manner that from labeled sugar chain A', one kind or plural kinds of product ion a is generated, and from labeled sugar chain B', one kind or plural kinds of product ion b is generated, and from labeled sugar chain C', one kind or plural kinds of product ion c is generated.

By detecting such product ion, it is possible to distinguish structural isomers (A, B, C, . . . ) from each other.

More specifically, when two kinds of sugar chains, sugar chain A and sugar chain B which are in relation of mutual structural isomers are analyzed as the sugar chains, structural analysis may be conducted in the following manner.

In a same manner as described above, by labeling with the use of the aforementioned labeling compound, labeled sugar chain A' is obtained from sugar chain A, and labeled sugar chain B' is obtained from sugar chain B.

Negative ions are measured by a mass spectrometer in a same manner as described above.

By conducting MS measurement of negative ions, molecular ions having the same (m/z) value are generated from the respective structural isomers. Taking this molecular ion as a precursor ion, MS/MS (or multistage MS of $MS^3$ or more) measurement is conducted, and a specific ion is detected for each of the structural isomers. Assuming that one kind or plural kinds of product ion a is generated from labeled sugar chain A', and one kind plural kinds of product ion b is generated from labeled sugar chain B', relation between product ions a and b is as follows. That is, from labeled sugar chain A', at least one of product ions b is not generated, and from labeled sugar chain B' at least one of product ions a is not generated; and also, combination of mass number differs between product ions a and product ions b. In this manner, negative ion is generated in reflection of very small difference in structure. Therefore, it becomes possible to readily distinguish structural isomers from each other which was impossible in conventional mass spectrometry.

When $MS^n$ analysis is used in the present basic step, this specific ion may usually be detected by $MS^2$ analysis, however, a new specific ion can be detected by conducting $MS^3$ analysis or further $MS^n$ analysis depending on the particular case. Detecting more specific ions in this manner is also desirable to obtain more specific information.

It is also possible to distinguish structural isomers, and identify partial or entire structure of structural isomer from information of detected ion. In particular, analyzing an ion specifically generated from a structural isomer may contribute to determination of important partial structure such as a minimum structure of a structure which is a determinant group of antigen or of a structure which is a key for expression of function in sugar chain. Of course, entire structure of structural isomer can be identified not only by analyzing such specific ion, but also by analyzing the ion that is commonly detected in structural isomers.

In the following, detailed explanation will be given for the case where a plural kinds of sugar chains are contained in a sample.

It is often the case that a biological sample is a mixture of various kinds of sugar chains. When the plural sugar chains contained in a sample are sugar chains mutually having different molecular weights, analysis can be readily conducted. For example, considering the case where a plural kinds of fucose containing sugar chains are contained in a sample, one sugar chain having one residue of fucose bound thereto while another sugar chain having two residues of fucose bound thereto. Such sugar chains mutually having different fucose binding numbers can be readily distinguished, identified and quantified by mass spectrometry because molecular weights are mutually different.

However, as previously described, a sugar chain can include a plurality of structural isomers having the same molecular weight and the same monosaccharide composition. The present basic step is advantageously used when plural kinds of sugar chains contained in a sample are in relation of mutual structural isomers. In the method of the present basic step, presence of other molecule in a sample on measurement will not influence on the phenomenon in which a particular product ion is specifically generated from a particular structural isomer. That is, ionization occurs dependently and specifically for individual structural isomer. Therefore, also in this case, analysis may be conducted according to the method as described above. That is, by detecting a product ion that is specifically generated from a particular structural isomer, quantification as well as identification of structural isomer is enabled.

For example, analysis may be conducted in the following manner. In the example of analysis method described below, description is given for quantification method, however, entire structure or partial structure of sugar chain can be identified by principally using information of product ion generated specifically from a particular structural isomer, as described above.

A sample containing plural kinds of structural isomers of sugar chain in known mixing ratio is prepared.

In the same manner as described above, plural kinds of sugar chains are labeled with the use of the aforementioned labeling compound to give a plural kinds of labeled structural isomers.

In the same manner as described above, negative ions are measured by a mass spectrometer.

A specific ion is detected for each of the plural kinds of labeled structural isomers by mass spectrometric measurement. By the specific ion obtained according to the present basic step for the structural isomers, the plural kinds of structural isomers can be distinguished.

As described above, when $MS^n$ analysis is used in the present basic step, the specific ion can usually be detected by $MS^2$ analysis, however, it is also preferred to detect more specific ions by conducting $MS^3$ analysis or further $MS^n$ analysis depending on the particular case, thereby obtaining more detailed information.

As described above, in the present basic step, presence of other molecule in a sample on measurement will not influence on the phenomenon in which a particular product ion is specifically generated from a particular structural isomer. Therefore, detected specific ions are detected in ion strength ratio reflecting mixing ratio of the structural isomers contained in the sample. Based on this fact, an ion specifically generated from a structural isomer may be used as an ion for quantification of the structural isomer.

Therefore, in the quantification analysis, specifically, an ion specifically generated from a structural isomer is determined as an ion for quantification of the structural isomer, and it is possible to find relation between ion strength of ion for quantification and known mixing ratio based on the known mixing ratio of plural structural isomers contained in the sample. For example, when structural isomers X and structural isomers Y are contained in the sample in a ratio which is the same with the above known mixing ratio, the strength ratio between particular ion x generated from structural isomer X and particular ion y generated from structural isomers Y is always identical; and such relation can be found that when an amount of structural isomers X relative to structural isomers Y in the sample changes, ion strength of ion x relative to ion y will change in multiple proportion to relative mixing amount.

As described above, information of the ion for quantification that is obtained by determining the ion and finding relation between the ion strength and a present ratio of structural isomer in the sample may be advantageously used in quantitative analysis in the case where a plurality of structural isomers are present in the sample in unknown mixing ratio. For example, the unknown mixing ratio may be calculated in the following manner.

A sample containing plural kinds of structural isomers of sugar chain in unknown mixing ratio is prepared.

In the same manner as described above, a plurality of structural isomers are labeled with a labeling compound to give plural kinds of labeled structural isomers.

In the same manner as described above, negative ions are measured by a mass spectrometer.

A specific ion is detected for each of the plural kinds of labeled structural isomers. Comparison is made for a set of ions having the same mass number, an ion detected in the above and an ion for quantification, and unknown mixing ratio is calculated from ion strength of the detected ion, based on the relation between ion strength of ion for quantification and mixing ratio in the sample, found in the aforementioned manner. In the manner as described above, quantification may be made for a plurality of structural isomers of sugar chain.

Identification of structure of sugar chain having the unknown structure in the present basic step may be achieved, for example, by obtaining a mass spectrometry result of the sugar chain having the unknown structure according to the method of the present basic step and comparing the mass spectrometry result with a mass spectrometry result of sugar chain having known structure. The followings are exemplary embodiments for carrying out identification of structure in this manner, however, the embodiments given herein also include the cases where plural kinds of structural isomers of sugar chain are analyzed as described above.

(1) Prepare a sample containing a sugar chain having the unknown structure.

Label the sugar chain having the unknown structure with a labeling compound, to give labeled sugar chain having the unknown structure.

Measure the labeled sugar chain having the unknown structure in negative mode by using a MALDI mass spectrometer.

(2) Separately, prepare a sample containing a sugar chain having known structure.

Label the sugar chain having known structure with a labeling compound, to give labeled sugar chain having known structure.

Measure the labeled sugar chain having known structure in negative mode by using a MALDI mass spectrometer.

(3) Compare mass spectrum of the labeled sugar chain having the unknown structure obtained in (1) and/or information obtained from the mass spectrum, with mass spectrum of the labeled sugar chain having known structure obtained in (2) and/or information obtained from the mass spectrum.

Here, information obtained from mass spectrum includes structural information of product ion itself, position on the precursor ion where fragmentation that generates its product ion occurred, putative information about liberated neutral molecule, and information derived from combination of these information.

In the above step (3), the sugar chain having the unknown structure may be determined to have the same structure as the sugar chain having known structure, if it is determined that entire peak in mass spectrum of the labeled sugar chain having the unknown structure and/or entire information obtained from the mass spectrum coincides with entire peak in mass spectrum of the labeled sugar chain having known structure and/or entire information obtained from the mass spectrum.

When the expression "entire mass spectrum" is used, the peak to be compared should contain at least a major peak (namely, a peak detected in a certain degree of ion strength) and/or a peak which is essential for analyzing the entire structure of sugar chain. When the expression "entire information obtained from mass spectrum" is used, the information to be compared should contain at least information essential for the entire structure of sugar chain.

The term "coincide" or "coincidence" allows error within the measurement range of mass spectrometer when mass number or ion strength of generated ion is compared. Further, when information about structure such as sugar chain sequence or position on sugar chain is compared, perfect coincidence is required.

In the above method, structure of entire sugar chain can be determined. However, a sugar chain having the unknown structure takes an extremely various kind of structures, while the number of kinds of sugar chain having known structure which is available as a standard is limited. It is sometimes the case that determination of only a minimum structure such as structure that is a determinant for antigen or structure that is a key for expression of function in the sugar chain suffices rather than clarifying the entire structure of the sugar chain. Determining such partial structure is important. In the present basic step, partial structure may be determined in the following manner.

That is, in the above step (3), if it is determined that a particular peak in mass spectrum of the labeled sugar chain having the unknown structure and/or a particular information obtained from the mass spectrum coincides with a particular peak in mass spectrum of the labeled sugar chain having known structure and/or a particular information obtained from the mass spectrum, the sugar chain having the unknown structure may be determined to have the same structure as the sugar chain having known structure in the particular part.

For example, in the above step (3), if it is determined that a partial peak in mass spectrum of the labeled sugar chain having the unknown structure and/or a partial information obtained from the mass spectrum coincides with an entire peak in mass spectrum of the labeled sugar chain having known structure and/or an entire information obtained from the mass spectrum, the sugar chain having the unknown structure may be determined to have the same structure as the sugar chain having known structure as its partial structure.

In the following, description will be given about data obtained by the method of the present basic step.

From the mass spectrum obtained by the method of the present basic step (namely, the mass spectrum obtained by labeling a sugar chain, and subjecting the obtained labeled sugar chain to measurement of negative ions by a MALD mass spectrometer), important information about the sugar chain is obtained. For example, structural information of product ion including product ion specifically generated from a structural isomer, position on the precursor ion where fragmentation that generates the product ion occurred, putative information about liberated neutral molecule, and structural information or quantitative information derived from combination of these information may be exemplified. A mass spectrum containing such important information can be utilized as data concerning sugar chain.

For example, with respect to a variety of sugar chains having known structures, a variety of mass spectrums are obtained using the method of the present basic step, and the obtained mass spectrums and/or information obtained from the mass spectrums may be stored as data sets. Further, such data sets may contain mass spectrums of those having structure that is proved by the method of the present basic step and/or information obtainable from such mass spectrums.

Data contained in such data sets may be used as structural data of sugar chain having known structure for comparison when a mass spectrometry result of a sugar chain having the unknown structure is compared with a mass spectrometry result of sugar chain having known structure to thereby determine the unknown structure in the manner as described above.

In the following, an effect of the present basic step will be described.

First, since stable generation of negative ion is enabled in mass spectrometry, it becomes possible to generate a sufficient amount of precursor ions for enabling multistage MS measurement, and to realize mass spectrometry with high sensitivity. Further, in a negative ion of labeled sugar chain, α-glycoside bond of fucose or sialic acid after neutralization is stable, so that information about bonding position of these can be obtained from the fact that generation amount of product ions from which such sugar chain is eliminated is relatively reduced.

Particularly, in the case that the biomolecule to be analyzed is sugar chain, since negative ions of labeled sugar chain are generated in reflection of very small structure, they exhibit effectiveness in distinguishing complicated and wide variety of structural isomers. Capability of distinguishing structural isomers is equivalent to ability to obtain important information telling attachment to a particular position in sugar chain via a particular bond.

Therefore, by applying the method described in the basic steps for a biomolecule involved in a particular disease as described in the present specification, it is possible to find markers involved in various diseases, and to diagnose various diseases. For example, since a binding position of fucose can be revealed by analyzing fucose-containing sugar chain using the present basic steps, it is possible to find a marker of disease in which the fucose-containing sugar chain is involved. Further, since it is possible to clarify whether a particular fucose bond is included in a sugar chain having the unknown structure based on information of disease marker, diagnosis of disease can be readily conducted.

It is further notable that by using the present basic steps, it becomes possible to identify and quantify structural isomers by detecting a structure specific ion even when plural kinds of structural isomers of sugar chain are contained in a sample. Requested in diagnosis of disease is to clarify which structural isomer is present in what amount rather than clarifying presence or absence of structural isomers, however, conventionally, operation of separating sugar isomers is very complicated and requires specialized technique. In diagnosis using a very small amount of biological sample, in particular, complicated and time-consuming separating operation is inappropriate. Therefore, the method of the present invention applying the present basic steps enables identification and quantification at high sensitivity while the structural isomers are still in mixture, so that slight change due to difference in expression of disease can be grasped. Additionally, since the amount of biological sample can be reduced, burden on subject is also reduced. Therefore, the method of the present invention can be a very practically useful method.

In the following, screening of disease marker and mass spectrometry of sample containing biomolecule will be described in detail. Analysis of biomolecule (structural analysis and quantitative analysis) may be achieved by the basic steps as described in the above, however, by application of the basic steps in the manner below, it becomes possible to search disease marker and conduct mass spectrometry of sample containing biomolecule (determination of presence/absence or degree of expression of particular disease, that is, determination of presence/absence, progression of particular disease, and/or diagnosis of therapeutic effect for the particular disease).

Method for screening disease marker to which the above-described method for analyzing biomolecule is applied will be explained.

(1) A sample containing biomolecule X derived from a subject affected by a particular disease is prepared. At this time, a biological sample collected from the subject may be directly used, or a sample may be prepared by conducting an appropriate process in chemical or enzymatic manner for obtaining biomolecule X from such biological sample as is already described in the basic steps. In this context, a biomolecule derived from a subject affected by a particular disease is represented by biolmolecule X, and biolmolecule X may also contain a plurality of biomolecules derived from the subject.

Biomolecule X is labeled with a labeling compound to obtain labeled biomolecule X'. The labeling compound and the labeling method are as already described in the basic steps.

The labeled biomolecule X' is subjected to measurement of negative ions by a MALDI mass spectrometer. Apparatus and matrix used for measurement, and measurement method as a whole are as already described in the basic steps.

(2) Separately, a sample containing biomolecule Y derived from a subject unaffected by the particular disease is prepared. Also at this time, a biological sample collected from the unaffected subject may be directly used, or a sample may be prepared by conducting an appropriate process in chemical or enzymatic manner for obtaining biomolecule Y from such biological sample as is already describe in the basic steps. Biomolecule Y may also contain a plurality of biomolecules derived from the unaffected subject.

Preferably, the sample containing biomolecule Y is in correspondence with the sample containing biomolecule X. For example, these samples are collected from the identical parts in the body of the affected subject and in the body of the unaffected subject, and prepared by conducting the same process as is necessary.

Biomolecule Y is labeled with a labeling compound in a same manner as is the case of biomolecule X, to obtain labeled biomolecule Y'.

The labeled biomolecule Y' is subjected to measurement of negative ions by a MALDI mass spectrometer as is the case with biomolecule X'.

(3) Mass spectrum of the labeled biomolecule X' obtained in (1) and/or information obtainable from the mass spectrum, with mass spectrum of the labeled biomolecule Y' obtained in (2) and/or information obtainable from the mass spectrum are compared.

As is already described in the basic steps, information obtained from mass spectrum includes structural information of product ion itself, position on the precursor ion where fragmentation that generates the product ion occurred, putative information about liberated neutral molecule, and information derived from combination of such information.

In the step (3), when the mass spectrums and/or information obtained from respective mass spectrums are different from each other, that is, when they are different from each other in particular mass spectrum and/or particular information, presence of a structure involved in a particular disease is ascertained Here, the phrase "mass spectrum peak and/or information differs between these samples" include both of the case where they differ in mass/charge, and the case where they differ in ion strength but have the same mass/charge.

Among mass spectrum peaks and/or information which are different in mass/charge, those that is included in mass spectrum of labeled biomolecule X' and/or information obtained from the mass spectrum and not included in mass spectrum of labeled biomolecule Y' and/or information obtained from the mass spectrum teach the structure involved in expression of particular disease.

Among mass spectrum peaks and/or information which are different in ion strength, those that is included in those detected strongly, in mass spectrum of labeled biomolecule X' and/or information obtained from the mass spectrum, than in mass spectrum labeled biomolecule Y' and/or mass information obtained from the mass spectrum also teach structure involved in expression of particular disease. In this case, significantly strong detection in information obtained from mass spectrum of labeled biomolecule X' and/or information obtained from the mass spectrum is preferred, and determination about degree of ion strength at this time may be appropriately made by those skilled in the art.

By analyzing structure involved in expression of disease from such mass spectrum and/or information obtained from the mass spectrum, it is possible to find a disease marker. Specifically, structure involved in expression of particular disease or structure of biomolecule X having such structure analyzed in such a manner may be determined as a structure of disease marker.

The disease marker obtained by the method of the present invention may be advantageously used for analysis of sample containing a biomolecule as will be described later. The disease marker of the present invention may be used for diagnosis of various disease as described in detail in explanation of biomolecule taking sugar chain as an example. Therefore, disease markers of the present invention include sugar chains involved in the variety of disease as described above. As such sugar chains, sugar chains having fucose and/or sialic acid, blood group antigen sugar chains are exemplified. Specifically, ABO blood group antigen sugar chains or Lewis system blood group antigen sugar chains are exemplified.

By analyzing a sample containing biomolecule using a disease marker found in such a manner, it is possible to determine the presence/absence of expression of particular disease or degree of expression for a subject for which affection by a particular disease is unknown, or a subject for which degree of disease regarding the particular disease is unknown. As is already described, biomolecules properly function while their expression level is controlled depending on the time and occasion, and when a part of structure of the molecule is deficient or changed, the function will be defective and a disease will be expressed. Therefore, the ability of the disease marker to determine presence/absence of expression or degree of expression of a particular disease implies the possibility of diagnosing presence/absence, progression degree of particular disease, or therapeutic effect for a particular disease.

The following is description of a method for analyzing a sample containing biomolecule. In analysis of a sample containing biomolecule according to the present invention, the analysis may be conducted by mass spectrometry, or by other methods than mass spectrometry.

That is, in the method for analyzing a sample containing biomolecule according to the present invention, a sample containing biomolecule derived from a subject is prepared, and presence/absence of expression or degree of the expression of a particular disease in the subject is determined.

The following is description for the case where analysis of biomolecule is conducted using mass spectrometry. As a disease marker in the method for analyzing a sample containing biomolecule using mass spectrometry, disease markers found by the method for screening disease marker of the present invention as described above, as well as disease markers found by methods other than the method of the present invention may also be used.

A sample containing biomolecule Z derived from a subject is prepared. The subject include: a subject for which affection to a particular disease is unknown; a subject affected by a particular disease, for which degree of progression of clinical condition is unknown; and a subject affected by a particular disease and receiving therapy for the particular disease, for which degree of therapeutic effect is unknown. Biomolecule Z may include a plurality of biomolecules derived from the subject.

Biomolecule Z is labeled with a labeling compound, to give labeled biomolecule Z'. The labeled biomolecule Z' is subjected to measurement of negative ions by a MALDI mass spectrometer.

Taking mass spectrum of disease marker and/or information obtained from the same as an index for presence/absence of a particular disease and/or degree of expression, mass spectrum of labeled biomolecule Z' and/or information obtained therefrom is examined. For example, presence/absence of expression of a particular disease may be determined from whether mass spectrum of biomolecule Z' and/or information obtained therefrom contains the same mass spectrum peak of the disease marker and/or information obtained therefrom. When mass spectrum of biomolecule Z' and/or information obtained therefrom contains the same mass spectrum peak of the disease marker and/or information obtained therefrom, degree of expression of the particular disease may also be determined from the ion strength.

In determining presence/absence or degree of expression of a particular disease, determination may made based on previously acquired mass spectrum about a disease marker and/or information obtained therefrom, or alternatively, determination may be made by conducting labeling and measuring operations for the disease marker in parallel with the labeling and measuring operations for the sample derived from the subject, and comparing the obtained mass spectrums and/or information obtained therefrom. In the method presented below, the details of each step are as described above.

(1) A sample containing biomolecule Z derived from a subject is prepared.

The biomolecule Z is labeled with a labeling compound, to give labeled biomolecule Z'.

The labeled biomolecule Z' is subjected to measurement of negative ions by a MALDI mass spectrometer.

(2) Separately, a disease marker is prepared.

The disease marker is labeled with a labeling compound, to give a labeled disease marker.

The labeled biomolecule Z' is subjected to measurement of negative ions by using a MALDI mass spectrometer.

(3) Mass spectrum of labeled biomolecule Z' obtained in the above (1) and/or information obtained from the mass spectrum are compared with mass spectrum of the disease marker obtained in the above (2) and/or information obtained from the mass spectrum, to determine absence/presence of expression of the particular disease in the subject, or degree of the expression.

When analysis of biomolecule is conducted by other methods than mass spectrometry (for example, histological stain, immunological measurement), analysis may be conducted using known methods except for using a disease marker found in the method for screening disease marker of the present invention.

EXAMPLES

The present invention will now be explained in more detail by way of examples, however, the present invention will not be limited by these examples.

Example 1

In Example 1, mass spectrometry was conducted for lacto-N-fucopentaose III.

(Labeling of Sugar Chain)

Lacto-N-fucopentaose III which is neutral sugar was labeled. For labeling, a method modified from the method of D. SUGAHARA, J. AMANO, and T. IRIMURA, ANALYTICAL SCIENCE, 19, 167-169 (2003) was used.

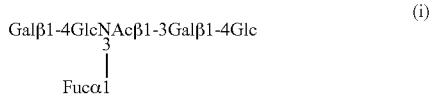

(i)

1 nmol of neutral sugar was added to a glass reaction tube with screw cap, and dried to solid. This reaction tube was added with a solution of 500 nmol PBH (Molecular Probes) dissolved in 20 microL of methanol, and 2 microL of acetic acid diluted in methanol (methanol:acetic acid=1:8 (v/v)), and the cap was fully closed. After thoroughly stirring the reaction solution in the reaction tube, the reaction was heated at 80° C. for 20 minutes, and added with 1M NaOH for neutralization. Then the reaction tube was added with 30 microL of 1.7M NaBH$_4$ solution and allowed to react for 30 minutes at 40° C., and further added with 10 microL of 1.7M NaBH$_4$ solution and allowed to react for 30 minutes at 40° C. The reaction tube was added with 400 microL of pure water and 400 microL of chloroform, and shaken well, and then left still. After removing the lower phase of chloroform, 400 microL of fresh chloroform was added and same extraction was carried out again. The upper phase was taken and dried, to give dried reaction product. Sep-pak C18 cartridge was washed with methanol, followed by pure water, and the dried reaction product was dissolved in pure water, and applied to the cartridge. After washing the cartridge with pure water, elution with acetonitrile-pure water (acetonitrile:pure water=6:4 (v/v)) was conducted to give eluate containing a target pyrene-labeled sugar. The eluate was dried to solid, and pyrene-labeled sugar was obtained. The obtained pyrene-labeled sugar was stored at −30° C. in the dark.

(Mass Spectrometry)

As a measurement sample, the obtained pyrene-labeled sugar was dissolved in pure water so that its concentration was 1 pmol/microL.

Separately, as another measurement sample, commercially available aminopyridine-labeled sugar (TAKARA BIO INC.) was prepared. This aminopyridine-labeled sugar was also dissolved in pure water so that 1 pmol/microL was realized.

0.4 microL of pyrene-labeled sugar solution (pyrene-labeled sugar 400 fmol), and 0.4 microL of aminopyridine-labeled sugar solution (aminopyridine-labeled sugar 400 fmol) were respectively applied on MALDI target plate.

As a matrix, DHBA was used. DHBA was dissolved in 40 v/v % acetonitrile solution in pure water so that its concentration was 12.5 mg/mL, and 0.5 microL therefrom was mixed with the respective labeled sugar solutions on the plate, and then dried to solid.

The obtained MALDI target plate was introduced into a MALDI-QIT-TOF mass spectrometer, AXIMA-QIT (Shimadzu/Kratos) and MS measurement was conducted in negative mode.

Mass spectrum obtained in this case is shown in FIG. 1. FIG. 1(a) is MS spectrum of pyrene-labeled sugar, and FIG. 1(b) is MS spectrum of aminopyridine-labeled sugar. In both spectrums, the horizontal axis represents (mass/charge) (m/z), and the vertical axis represents relative ion strength (this applies to every mass spectrum described below in this specification). Further in FIG. 1, every peak is represented on the basis of ion strength of molecular ion [M−H]$^-$ of pyrene-labeled sugar of 100.

As shown by these spectrums, only molecular ion m/z 1138 [M−H]$^-$ in FIG. 1(a), and only molecular ion m/z 930 [M−H]$^-$ in FIG. 1(b) are strongly detected, and decomposed ions were little detected. This demonstrates that sufficient precursor ions are generated for use in MS/MS measurement for obtaining more specific structural information.

Taking FIG. 1(a) for pyrene-labeled sugar as an example among these spectrums, from S/N ratio of measurement result, it can be supposed that detection limit is about 10 fmol. To the contrary, conventional detection limit of non-labeled sugar chain is 10 pmol. This suggests that detection is possible only in 1/1000 amount.

In this way, it is possible to detect negative molecular ion [M−H]$^-$ without adding acidic substance to matrix as is the conventional case, and detection is possible only in a 1/1000 amount of conventional detection limit of non-labeled sugar chain. This would be attributable to the fact that high efficient ionization and ionization which generate stable ions are realized by pyrene-labeling.

Also by using a commercially available concentration plate, the sensitivity may be improved 10 times to 20 times, so that this can be satisfactorily applied to analysis of a very small amount of biological sample.

Example 2

In Example 2, mass spectrometry was conducted for three kinds of structural isomers of monofucosyl lacto-N-hexaose.

Each of structural isomers of monofucosyl lacto-N-hexaose, MFLNH-I (Formula (ii)), MFLNH-II, (Formula (iii)) and MFLNH-III (Formula (iv)) was subjected to pyrene-labeling, and MS measurement and MS/MS measurement in negative mode using a MALDI-QIT-TOF mass spectrometer in a same manner as described in Example 1.

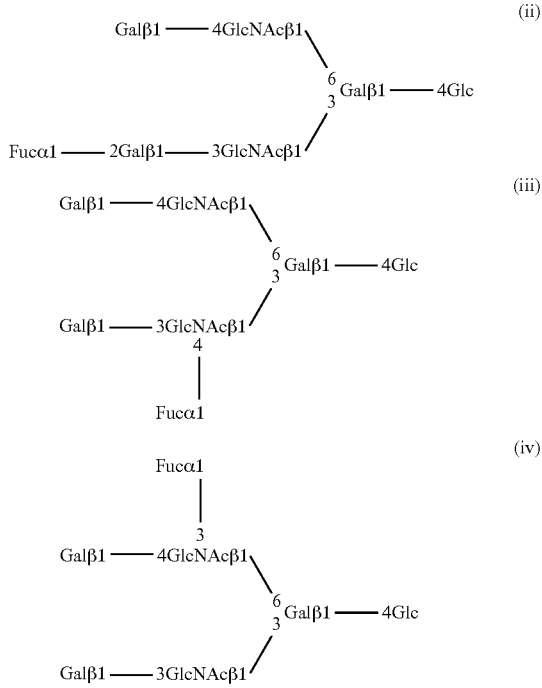

As a result of MS measurement, in every spectrum, m/z 1503 [M–H]⁻ was strongly detected as a unique parent ion, and decomposed ions were little detected (data not shown).

Figure 2:
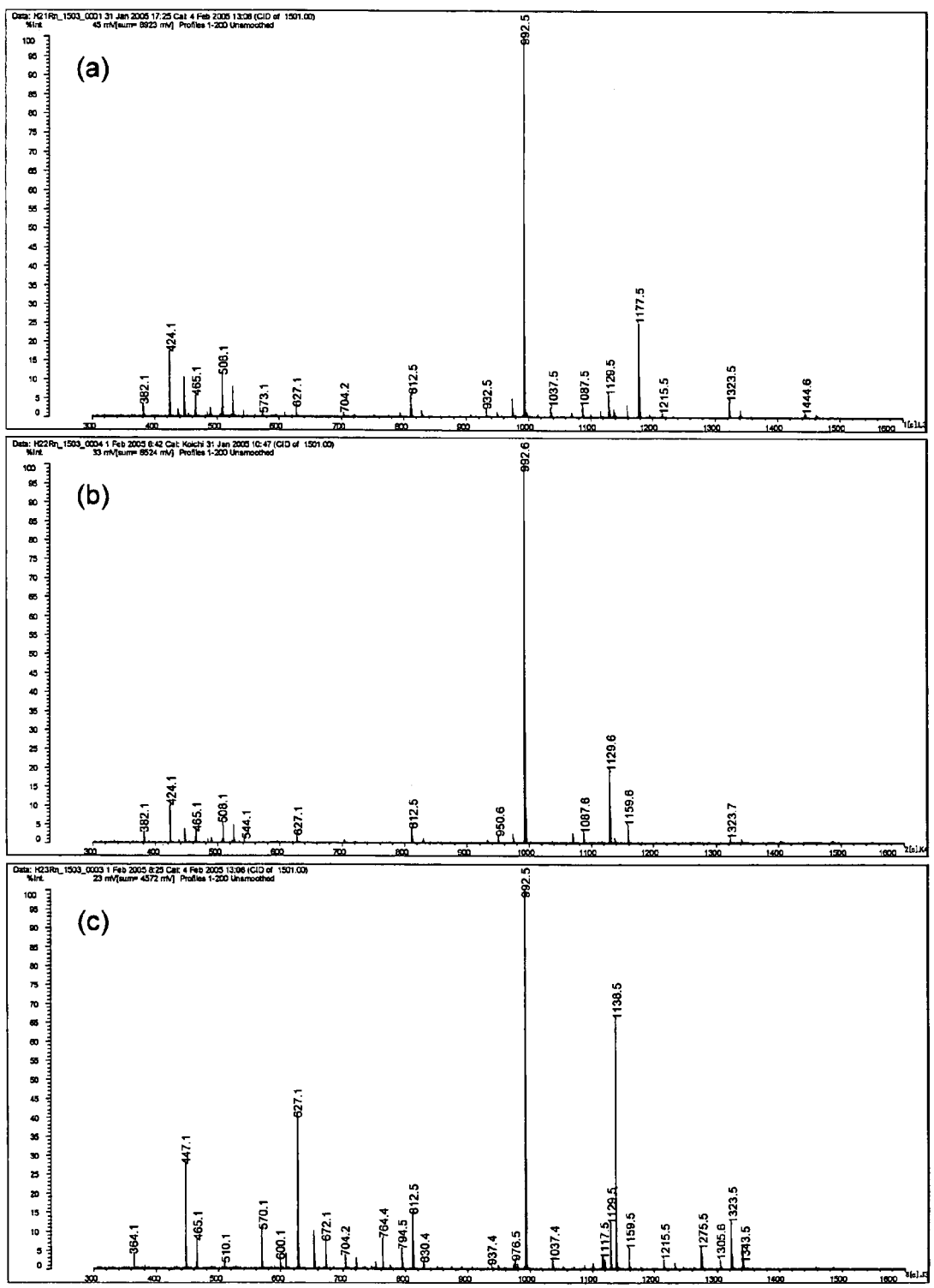
FIGS. 2 are (a) a negative ion $MS^2$ spectrum of pyrene-labeled MFLNH-I, (b) a negative ion $MS^2$ spectrum of pyrene-labeled MFLNH-II, and (c) a negative ion $MS^2$ spectrum of pyrene-labeled MFLNH-III.

FIG. 2 shows mass spectrums obtained by MS/MS measurement using ion m/z 1503 detected in MS measurement as a precursor ion. FIG. 2(a) is MS/MS spectrum of pyrene-labeled MFLNH-I, FIG. 2(b) is MS/MS spectrum of pyrene-labeled MFLNH-II, and FIG. 2(c) is MS/MS spectrum of pyrene-labeled MFLNH-III.

As can be seen from these spectrums, peak patterns which are completely different from one another were observed in MS/MS spectrums. Values of m/z of major ions detected in FIGS. 2(a) to 2(c) are shown in Table 1. In Table 1, the mark "+" represents that the ion is detected at ion strength of equal to or more than 10%, and the mark "±" represents that the ion is detected at ion strength of equal to or less than 10%. As shown in Table 1, for example, product ion of m/z 1177 is detected only from pyrene-labeled MFLNH-I, and product ion of m/z 1138 is detected only from pyrene-labeled MFLNH-III. In this way, an ion species which is peculiar for a particular isomer and is not generated from other isomers is observed.

As will be described in Comparative example 1, when positive ion measurement is conducted rather than the negative ion measurement as in the preset example, product ion from which fucose is liberated is mainly detected. If such a product ion species from which fucose is liberated is generated in the negative ion measurement of Example 2, the ion species would be detected at m/z 1357. However, in Example 2, such ion species was not detected at all.

In this manner, when measurement of negative ions is conducted, an ion species which is peculiar to individual isomer is observed, revealing that measurement of negative ion allows easy determination and identification of isomer structure.

TABLE 1

| m/z | MFLNH-I | MFLNH-II | MFLNH-III |
|---|---|---|---|
| 1177 | + | | |
| 1138 | | | + |
| 1129 | ± | + | ± |
| 992 | + | + | + |
| 812 | ± | ± | + |
| 627 | ± | ± | + |
| 570 | | | + |
| 447 | + | | + |
| 424 | + | + | |
| 382 | ± | ± | |

Further, information which is useful for identification of general structure is also obtained.

For example, as shown in Table 1, product ion m/z 424 was generated from pyrene-labeled MFLNH-I and pyrene-labeled MFLNH-II, and product ion m/z 570 was generated from pyrene-labeled MFLNH-III. We ascertained that these product ions are generated when a side chain is attached to 6-position of galactose.

It is also clarified that difference between product ion m/z 424 generated from pyrene-labeled MFLNH-I and pyrene-labeled MFLNH-II, and product ion m/z 570 generated from pyrene-labeled MFLNH-III corresponds to one fucose residue. That is, product ion of m/z 424 does not have a fucose residue, while product ion of m/z 570 has one fucose residue. This demonstrates that a fucose residue is not bound on the 6-side chain of precursor ion from which product ion of m/z 424 is generated, and one fucose residue is bound on the 6-side chain of precursor ion from which product ion of m/z 570 is generated.

Product ion of m/z 1177 generated exclusively from pyrene-labeled MFLNH-I can be considered as ion that is generated by loosing Fuc-Gal, from difference in m/z from precursor ion. That is, it can be understood that a precursor ion from which such product ion is generated has Fucα1-2Gal bond. Therefore, it is possible to readily distinguish pyrene-labeled MFLNH-I from pyrene-labeled MFLNH-II.

Therefore, it was found that by distinguishing a product ion which is specifically generated from an isomer, and calculating difference in m/z between precursor ion and product ion, sugar chain structure can be identified.

Comparative Example 1

In Comparative example 1, same operations as described in Example 2 were executed except that MS measurement and MS/MS measurement were conducted with positive ion.

As a result of MS measurement, m/z 1528 [M+Na]⁺ was detected as a parent ion in every spectrum.

Figure 3:
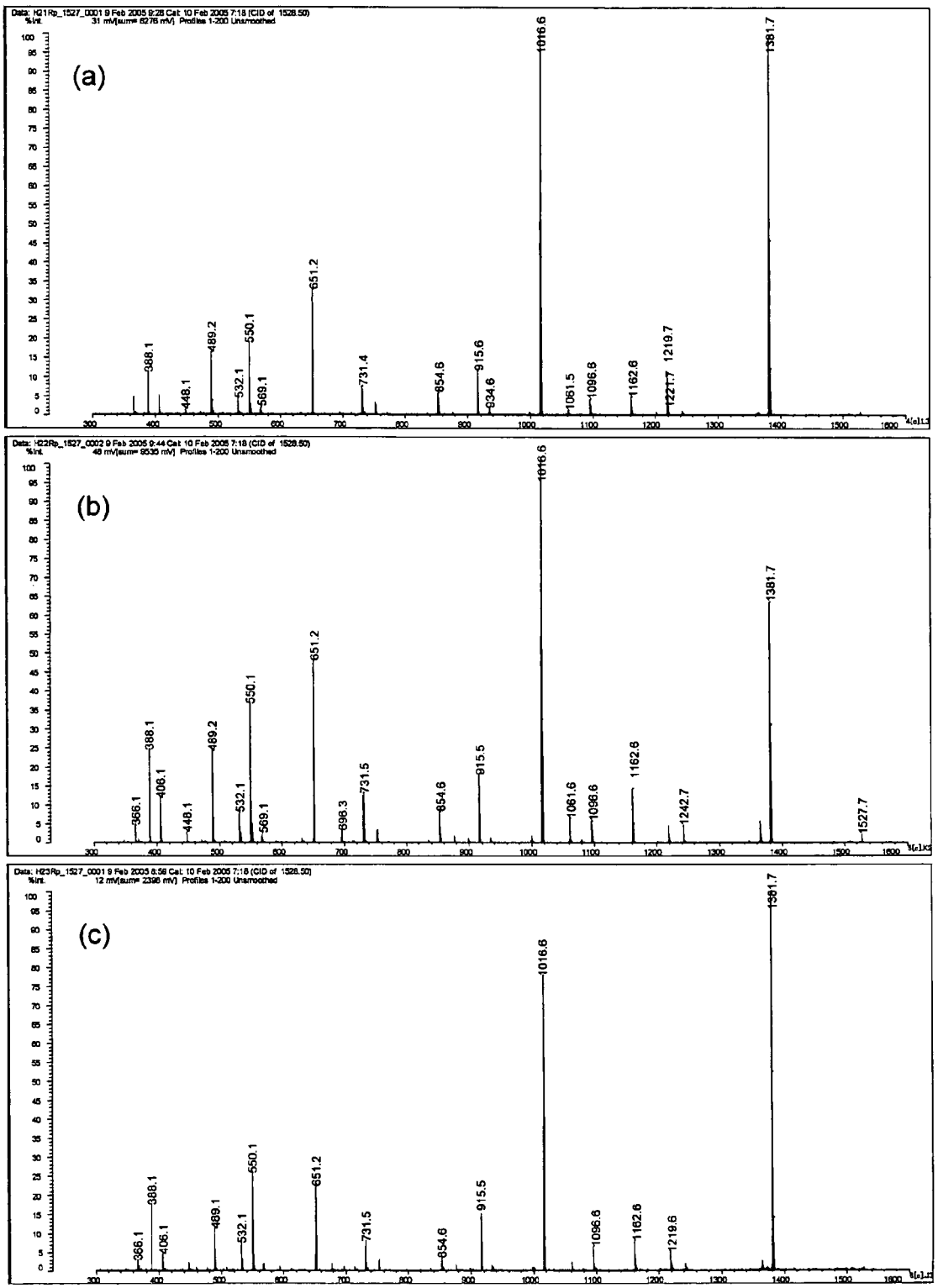
FIGS. 3 are (a) a positive ion $MS^2$ spectrum of pyrene-labeled MFLNH-I, (b) a positive ion $MS^2$ spectrum of pyrene-labeled MFLNH-II, and (c) a positive ion $MS^2$ spectrum of pyrene-labeled MFLNH-III.

FIG. 3 shows mass spectrums obtained by MS/MS measurement using ion m/z 1528 detected in MS measurement as a precursor ion. FIG. 3(a) is MS/MS spectrum of pyrene-labeled MFLNH-I, FIG. 3(b) is MS/MS spectrum of pyrene-labeled MFLNH-II, and FIG. 3(c) is MS/MS spectrum of pyrene-labeled MFLNH-III.

As shown in FIG. 3, in any of three obtained MS/MS spectrums, product ion species m/z 1381 having a common structure from which fucose is liberated was significantly detected. This indicates that fucose bond is extremely unstable in positive ion. Regarding other product ions respectively generated from three isomers, almost the same species was detected except that the relative strength differs. This demonstrates that it is difficult to distinguish three isomers from one another.

Example 3

In Example 3, more detailed mass spectrometry was conducted for two structural isomers of monofucosyl lacto-N-hexaose.

Figure 4:
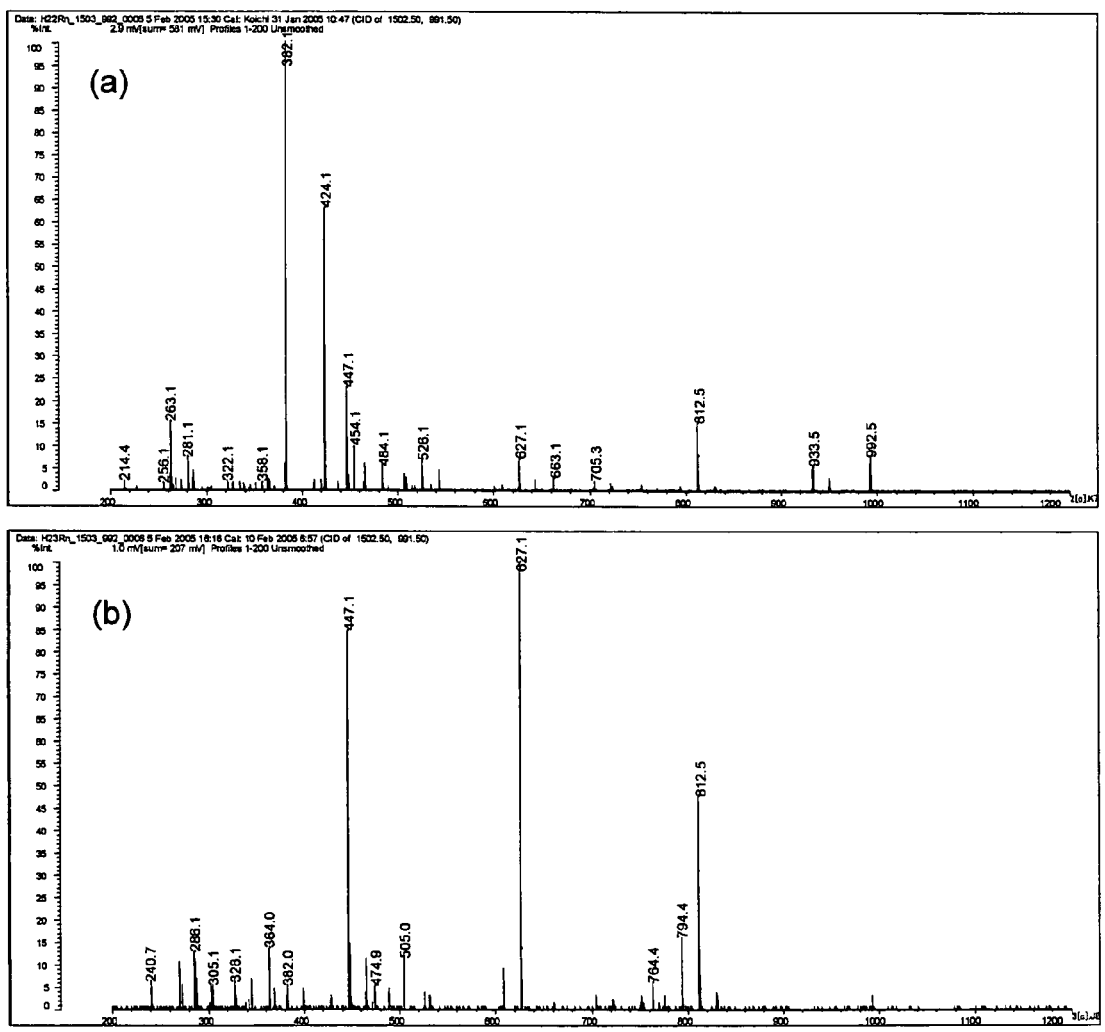
FIGS. 4 are (a) a negative ion $MS^3$ spectrum of pyrene-labeled MFLNH-II, and (b) a negative ion $MS^3$ spectrum of pyrene-labeled MFLNH-III.

Using MFLNH-II and MFLNH-III, operations up to MS/MS measurement was conducted in the same manner as in Example 2. Taking product ion m/z 992 which is obtained at highest ion strength and commonly obtained in the obtained MS/MS spectrums as a precursor ion, each $MS^3$ measurement was conducted. FIG. 4 shows obtained mass spectrums. FIG. 4(a) is $MS^3$ spectrum of pyrene-labeled MFLNH-II, and FIG. 4(b) is $MS^3$ spectrum of pyrene-labeled MFLNH-III.

As shown in FIG. 4(a), m/z 388, 424, 447 and so on were detected as product ions derived from pyrene-labeled MFLNH-II, while as shown in FIG. 4(b), m/z 447, 627, 812 and so on were detected as product ions derived from pyrene-labeled MFLNH-III. As is apparent from these spectrums, combination of significantly appearing product ions differs between different isomers, and is easily distinguishable. It was demonstrated that ions of m/z 992 detected in MS/MS measurement commonly appear in different isomers, however, these ions have different structures generated by fragmentations at different positions in precursor ion, although they have the same mass number. This more clearly demonstrates that negative ion is generated in reflection of very small difference in structure.

Example 4

In Example 4, mass spectrometry was conducted for sialic acid containing sugar chain (v) as shown below.

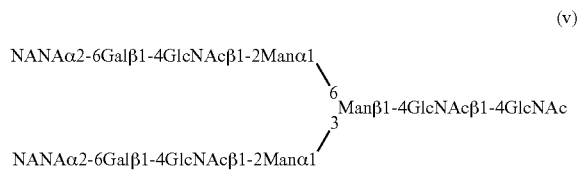

(v)

Figure 5:
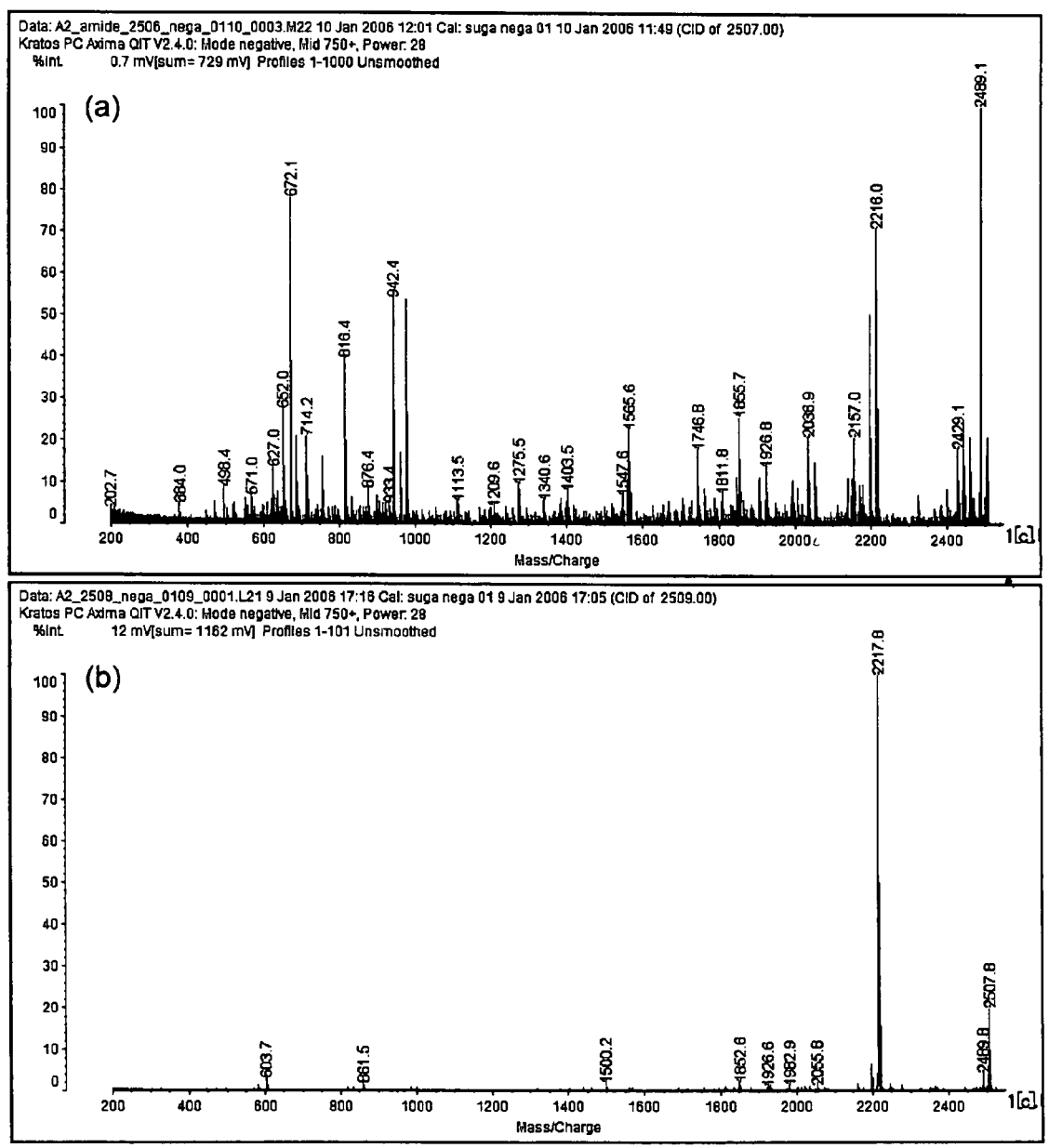
FIGS. 5 are (a) a negative ion MS² spectrum of pyrene-labeled sugar chain containing amidated sialic acid, and (b) a negative ion MS² spectrum of pyrene-labeled sugar chain containing non-amidated sialic acid.

Labeling of sugar chain was conducted in a same manner as described in Example 1, and pyrene-labeled sugar was obtained. The obtained pyrene-labeled sugar was subjected to the following neutralization process. Concretely, 1 μL of 10 pmol/μL pyrene-labeled sugar aqueous solution was added to 12.5 μL of 1M $NH_4Cl$ aqueous solution, and then added with 7.5 μL of 1M 4-(4,6-dimethoxy-1,3,5-triazine-2-yl)-4-methyl morphorinium chloride aqueous solution, and then reaction was allowed at 50° C. for 24 hours. By this neutralization process, hydroxyl group of sialic acid was amidated, and converted to carbamoyl group. The sugar chain having experienced the neutralization process was subjected to the operations as described in Example 1, to prepare a sample for mass spectrometry on a MS plate, and MS measurement was conducted in negative mode using a mass spectrometer. As $[M-H]^-$ ion, m/z 2505.9 was detected. Further, MS/MS measurement was conducted while taking m/z 2505.9 as a precursor ion to obtain ions which are important for structure identification such as C-series ion (m/z 672.1), B-series ion (m/z 816.4), and A-series ion (m/z 876.4) including amidated sialic acid as shown in FIG. 5(a). In this way, effectiveness of conducting negative MS/MS measurement after neutralizing a sugar chain containing sialic acid was proved.

Comparative Example 2

In Comparative example 2, same operations as described in Example 4 were conducted except that sialic acid containing sugar chain (v) was not subjected to neutralization process. As a result of MS measurement, m/z 2507.9 was detected as $[M-H]^-$ ion. Then MS/MS measurement was conducted while selecting m/z 2507.9 as precursor ion, and ions in which one molecule of sialic acid was liberated were mainly generated as shown in FIG. 5(b) and mass spectrum that provides useful information was not observed.

Example 5

In Example 5, mass spectrometry was conducted for a mixture containing at least one of two kinds of structural isomers of monofucosyl lacto-N-hexaose (MFLNH-I and MFLNH-III).

MFLNH-I has blood group H antigen structure, and includes fucose bond of prostatic cancer antigen PSA derived from cancer cell. MFLNH-III has Lewis X antigen structure, and includes fucose bond expressed in haptoglobin and CA125 which are glycoproteins derived from ovary cancer patient.

MFLNH-I and MFLNH-III were respectively labeled with pyrene in the manner as described in Example 1, to obtain pyrene-labeled MFLNH-I and pyrene-labeled MFLNH-III. Samples for measurement were prepared so that they contain pyrene-labeled MFLNH-I and pyrene-labeled MFLNH-III in the ratios of 10:0, 8:2, 6:4, 4:6, 2:8, and 0:10, respectively.

Here, an assumption is made that a particular disease is associated with expression of Lewis X sugar chain structure, and the expression level is correlated with progression of clinical condition and degree of malignancy. Three kinds of samples are assumed: sample derived from subject not affected by particular disease (Lewis X expression 20%), sample derived from subject onset particular disease (Lewis X expression 40%), and sample derived from subject affected by particular disease and having progressed clinical condition (Lewis X expression 80%). Thus, taking notice of Lewis X sugar chain structure, for example, the mixed samples prepared above containing pyrene-labeled MFLNH-I and pyrene-labeled MFLNH-III in ratios of 8:2, 6:4 and 2:8 are respectively correspond to samples of subjects who have different expression states of Lewis X antigen assumed above.

On the other hand, an assumption is made that a particular disease is associated with expression of blood group H antigen structure, and the expression level is correlated with progression of clinical condition and degree of malignancy. Three kinds of samples are assumed: sample derived from subject affected by particular disease and having progressed clinical condition (blood group H expression 80%), sample derived from subject onset particular disease (blood group H expression 60%), and sample derived from subject not affected by particular disease (blood group H expression 20%). Thus, taking notice of blood group H antigen structure, for example, the mixed samples prepared above containing pyrene-labeled MFLNH-I and pyrene-labeled MFLNH-III in ratios of 8:2, 6:4 and 2:8 are also respectively correspond to samples of subjects who have different expression states of blood group H antigen structure assumed above.

For these six kinds of measurement samples, MS/MS measurement (precursor ion: m/z 1503) was conducted in the same manner as descried in Example 1.

Figure 6:
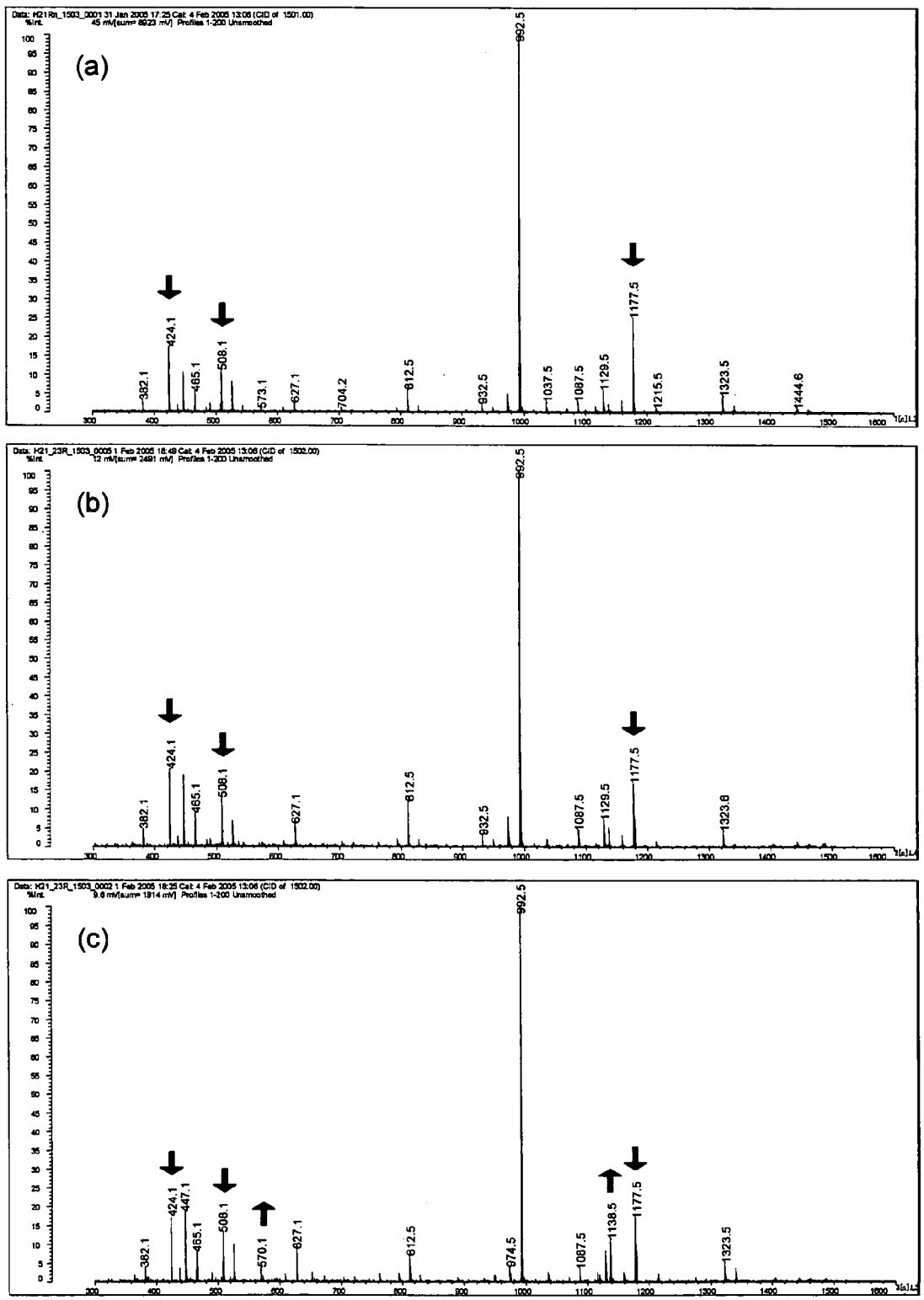
FIGS. 6 are (a) a negative ion MS² spectrum of a sample containing pyrene-labeled MFLNH-I and pyrene-labeled MFLNH-III in a ratio of 10:0, (b) a negative ion MS² spectrum of a mixed sample containing in a ratio of 8:2, and (c) a negative ion MS² spectrum of a mixed sample containing in a ratio of 6:4.
Figure 7:
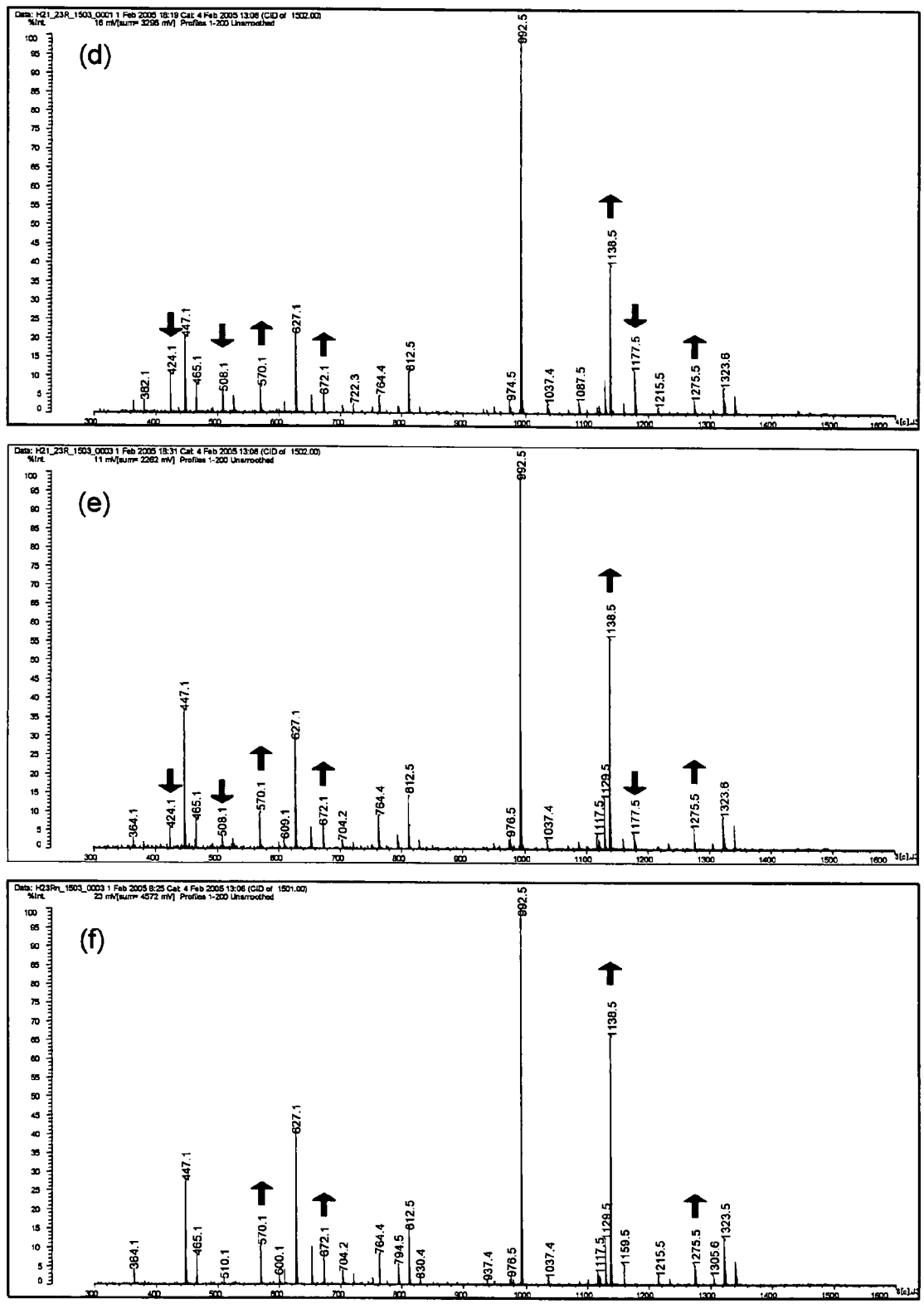
FIGS. 7 are (d) a negative ion MS² spectrum of a sample containing pyrene-labeled MFLNH-I and pyrene-labeled MFLNH-III in a ratio of 4:6, (e) a negative ion MS² spectrum of a mixed sample containing in a ratio of 2:8, and (f) a negative ion MS² spectrum of a mixed sample containing in a ratio of 0:10.

Obtained mass spectrums are shown in FIG. 6 and FIG. 7. FIG. 6(a) is MS/MS spectrum of a sample containing only pyrene-labeled MFLNH-I, FIG. 6(b) is MS/MS spectrum of a mixed sample containing pyrene-labeled MFLNH-I and pyrene-labeled MFLNH-III in mixing ratio of 8:2, FIG. 6(c) is MS/MS spectrum of a mixed sample containing pyrene-labeled MFLNH-I and pyrene-labeled MFLNH-III in mixing ratio of 6:4, FIG. 7(d) is MS/MS spectrum of a mixed sample containing pyrene-labeled MFLNH-I and pyrene-labeled MFLNH-III in mixing ratio of 4:6, FIG. 7(e) is MS/MS spectrum of a mixed sample containing pyrene-labeled MFLNH-I and pyrene-labeled MFLNH-III in mixing ratio of 2:8, and FIG. 7(f) is MS/MS spectrum of a sample containing only pyrene-labeled MFLNH-III.

As shown in FIGS. 6(a) to 6(c) and FIGS. 7(d) to 7(f), ion strength of particular ion changes as the mixing ratio of mixed sample changes. As to product ions m/z 1177, 508, 424 (marked with down-pointing arrows in Figs), ion strength decreases as the abundance ratio of pyrene-labeled MFLNH-I reduces, and it can be determined as being inversely correlated with progression of clinical condition of particular disease when Lewis X sugar chain structure is noticed. Also, as to product ions m/z 1275, 1138, 764, 570 (marked with up-pointing arrows in Figs), ion strength increases as the abundance ratio of pyrene-labeled MFLNH-III increases, and it can be determined as being correlated with progression of clinical condition of particular disease when Lewis X sugar chain structure is noticed.

On the other hand, for ascertaining this result, mass spectrums of sample containing only pyrene-labeled MFLNH-I and sample containing only pyrene-labeled MFLNH-III among the mass spectrums obtained in the above Example 2 (FIGS. 2(a) and 2(c)) were more completely examined, to find difference in presence/absence of 18 kinds of ions. In other words, ions that were observed in pyrene-labeled MFLNH-I but not in pyrene-labeled MFLNH-III were m/z 1177, 1087, 932, 508, 424, 382. On the other hand, ions that were observed in pyrene-labeled MFLNH-III but not in pyrene-labeled MFLNH-I were m/z 1343, 1305, 1275, 1138, 1117, 794, 764, 672, 654, 600, 570, 364.

Therefore, in FIGS. 6 and 7, it can be ascertained that the ions in which ion strength increases with increase in abundance ratio of pyrene-labeled MFLNH-III are generated from pyrene-labeled MFLNH-III, while the ions in which ion strength decreases with decrease in abundance ratio of pyrene-labeled MFLNH-I are generated from pyrene-labeled MFLNH-I.

Like this, showing correlation between ion strength and abundance ratio in mixture suggests that presence of other molecule on measurement sample will not influence on the phenomenon that a particular product ion is specifically generated from a particular structural isomer. Since specific ionization occurs independently for individual structural isomers, even if a measurement sample is a mixture of structural isomers, identification of structural isomer can be achieved by detecting a product ion specifically occurring from a particular structural isomer. For example, it can be found that, between samples containing biologically important antigen structures, product ions which are different from each other can be obtained. And by obtaining such product ions, it is possible to determine presence of a molecule which will be a marker for a particular disease in the sample.

Further, from specifically generated product ion and its strength, structural isomers can be separated and quantified. For example, detecting product ions which are different from each other between samples containing biologically important antigen structures will indicate progression of clinical condition and therapeutic efficiency of particular disease, as well as analysis of such structural information allows identification of marker molecule. Further, from such specifically generated ion species and its strength, separation and quantification of structural isomers, or determination of degree of expression of disease are enabled.

As for a concrete method for estimating abundance of each structural isomer from measurement result, the method described in Brown, C. W, et al. Anal. Chem., Vol. 54, No. 9, pp 1472 (1982), or Yasuo Iida et al., BUNSEKI KAGAKU, Vol. 32, pp 401 (1983) may be followed. That is, these documents disclose a quantification method concerning absorption photometry, and such method may be directly applied to mass spectrometry by replacing wavelength by mass number, absorbance by ion strength in the descriptions of these documents. By using such a method, application to N components is possible (that is, application to a mixed sample containing two or more structural isomers is also possible).

From these, it can be concluded that even when labeling and negative ion measurement are conducted in a same manner for a sample actually collected from a subject affected by lung cancer or ovary cancer in which Lewis X antigen is expressed, and for a sample actually collected from an unaffected subject, products ion that are different from each other are detected in the respective mass spectrometry results as shown in FIGS. 6 and 7, and information about disease marker is obtained.

It is also concluded that in conducting same labeling and negative ion measurement for a subject for which affected condition by particular disease is unknown, information about the disease (information about affection or un-affection of subject, progression degree of disease, efficacy of therapy and the like) can be obtained by conducting separation, quantification and the like described above based on information of disease marker.

As is already mentioned in Comparative example 1, according to the measurement results of positive ions of pyrene-labeled MFLNH-I and pyrene-labeled MFLNH-III, identical product ions are detected in the respective spectrums. More detailed examination revealed that all of detected 20 kinds of ions are common. Therefore, even when a positive ion is measured for a sample of such as the present example, product ion which shows correlation with ion strength and abundance ratio in mixture is not generated. In such a case, therefore, screening for markers is different.

The above-described Examples show concrete modes within the scope of the present invention, however, the present invention can be carried out in various other modes. Therefore, the above-described Examples are merely illustrative in all respects, and must not be construed as being restrictive. Further, the changes that fall within the equivalents of the claims are all within the scope of the present invention.

The invention claimed is:

1. A method of negative-ion MALDI analysis of neutral labeled sugar chain comprising the steps of:
preparing a sample containing a neutral sugar chain;
labeling the neutral sugar chain with a labeling compound having a fundamental skeleton of aromatic selected from the group consisting of pyrene, benzene, and pyridine and comprising at least one selected from the group consisting of amino group and carboxylic acid hydrazide group to obtain a neutral labeled sugar chain;
wherein the neutral sugar chain contains fucose; or
preparing a sample containing an acidic sugar chain;
neutralizing and labeling the acidic sugar chain with a labeling compound having a fundamental skeleton of aromatic selected from the group consisting of pyrene, benzene, and pyridine to obtain a neutral labeled sugar chain;

wherein the acidic sugar chain contains sialic acid; and
subjecting the neutral labeled sugar chain to negative ion MALDI analysis.

2. The method according to claim 1, wherein the sample contains neutral or acidic sugar chains that are mutually structural isomers (A, B, C, . . . ), wherein subjecting the neutral labeled sugar chains (A', B', C', . . . ) to negative ion MALDI analysis comprises performing $MS^2$ or $MS^3$ measurement by using MALDI-QIT-TOF mass spectrometer which produces structurally different ions (a, b, c, . . . ) that are specifically generated from the respective neutral labeled sugar chains (A', B', C', . . . ), thereby distinguishing the sugar chains (A, B, C, . . . ); from one another.

3. The method according to claim 2, wherein by conducting structure analysis for each of the ions (A, B, C, . . . ), an entire structure or a partial structure of the sugar chains (A, B, C, . . . ) is respectively identified.

4. The method according to claim 1, wherein the sample contains plural kinds of structural isomers of neutral or acidic sugar chain in a known mixing ratio, and wherein subjecting the plural kinds of neutral labeled structural isomers to negative ion MALDI analysis comprises performing $MS^2$ or $MS^3$ measurement by using MALDI-QIT-TOF mass spectrometer which produces ions specifically generated from the respective plural kinds of neutral labeled structural isomers, thereby analyzing the plural kinds of structural isomers of sugar chain.

5. The method according to claim 4, wherein
by conducting structure analysis for the detected specifically generating ions, an entire structure or a partial structure of each of the plural kinds of structural isomers of sugar chain is identified, and/or
the detected specifically generating ions are determined as ions for quantification of the plural kinds of structural isomers, and relation between ion intensity of the determined ion and the known mixing ratio is found.

6. The method according to claim 5, wherein the method further comprises performing the same steps, as recited in claim 5, for a second sample,
wherein the second sample contains plural kinds of structural isomers of neutral or acidic sugar chain in an unknown mixing ratio, and wherein subjecting the plural kinds of neutral labeled structural isomers to negative ion MALDI analysis comprises performing $MS^2$ or $MS^3$ measurement by using MALDI-QIT-TOF mass spectrometer which produces ions specifically generating from the respective plural kinds of neutral labeled structural isomers, thereby analyzing the plural kinds of structural isomers of sugar chain,
wherein by conducting structure analysis for the detected specifically generating ions, an entire structure or a partial structure of each of the plural kinds of structural isomers of sugar chain is identified, and/or
from ion intensity of detected specifically generating ion, the unknown mixing ratio is calculated based on the relation found for the known sample.

7. The method according to claim 1, wherein the sample contains one kind or plural kinds of neutral or acidic sugar chain having an unknown structure wherein, separately, a sample containing one kind or plural kinds of neutral or acidic sugar chain having a known structure is prepared, and
wherein subjecting both of the samples to negative ion MALDI analysis comprises performing $MS^2$ or $MS^3$ measurement by using MALD-QIT-TOF mass spectrometer,
wherein mass spectrum of the neutral labeled sugar chain having the unknown structure and/or information obtained from the mass spectrum is/are compared with mass spectrum of the neutral labeled sugar chain having the known structure and/or information obtained from the mass spectrum, to analyze the sugar chain having the unknown structure.

8. The method according to claim 7, wherein it is ascertained that an entire mass spectrum peak of the neutral labeled sugar chain having the unknown structure and/or an entire information obtained from the mass spectrum coincides with an entire mass spectrum peak of the neutral labeled sugar chain having the known structure and/or an entire information obtained from the mass spectrum, thereby the sugar chain having the unknown structure is determined to have the same structure as the sugar chain having the known structure.

9. The method according to claim 7, wherein it is ascertained that a particular peak in mass spectrum of the neutral labeled sugar chain having the unknown structure and/or particular information obtained from the mass spectrum coincides with a particular peak in mass spectrum of the neutral labeled sugar chain having the known structure and/or particular information obtained from the mass spectrum, thereby the sugar chain having the unknown structure is determined to have the same structure as the sugar chain having the known structure as a partial structure.

10. The method to claim 1, wherein the labeling compound used for conducting the labeling is selected from the group consisting of pyrenebutanoic acid hydrazide, aminopyrene, 2-aminopyridine, 2-aminobenzene, and amino benzoic acid ester.

11. A method for screening disease marker, comprising the steps of:
(1) preparing a sample containing a biomolecule X having a neutral sugar chain to be analyzed derived from a subject affected by a particular disease;
labeling the neutral sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule X' having a neutral labeled sugar chain;
wherein the neutral sugar chain contains fucose;
subjecting the biomolecule X' having the neutral labeled sugar chain to negative ion MALDI analysis comprises performing $MS^2$ or $MS^3$ measurement by using a MALDI-QIT-TOF mass spectrometer,
(2) separately, preparing a sample containing a biomolecule Y having the neutral sugar chain to be analyzed derived from a subject unaffected by the particular disease;
labeling the neutral sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule Y' having a neutral labeled sugar chain;
wherein the neutral sugar chain contains fucose;
subjecting the biomolecule Y' having the neutral labeled sugar chain to negative ion MALDI analysis comprises performing $MS^2$ or $MS^3$ measurement by using a MALDI-QIT-TOF mass spectrometer; or
(1) preparing a sample containing a biomolecule X having an acidic sugar chain to be analyzed derived from a subject affected by a particular disease;
neutralizing and labeling the acidic sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule X' having a neutral labeled sugar chain;

wherein the acidic sugar chain contains sialic acid;

subjecting the biomolecule X' having the neutral labeled sugar chain to negative ion MALDI analysis comprises performing $MS^2$ or $MS^3$ measurement by using a MALDI-QIT-TOF mass spectrometer;

(2) separately, preparing a sample containing a biomolecule Y having the acidic sugar chain to be analyzed derived from a subject unaffected by the particular disease;

neutralizing and labeling the acidic sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule Y' having a neutral labeled sugar chain;

wherein the acidic sugar chain contains sialic acid;

subjecting the biomolecule Y' having the neutral labeled sugar chain to negative ion MALDI analysis comprises performing $MS^2$ or $MS^3$ measurement by using a MALDI-QIT-TOF mass spectrometer; and (3) comparing mass spectrum of the biomolecule X' having the neutral labeled sugar chain obtained in (1) and/or information obtained from the mass spectrum, with mass spectrum of the biomolecule Y' having the neutral labeled sugar chain obtained in (2) and/or information obtained from the mass spectrum, to find mass spectrum peaks and/or information which are mutually different, thereby ascertaining presence of a structure involved in expression of the particular disease.

12. The method for screening disease marker according to claim 11, further comprising, (4) analyzing mass spectrum peaks or information obtained from the mass spectrum peaks found in (3), (5) picking up the following mass spectrum peaks or information (a) or (b), (a) mass spectrum peaks or information having different mass/charge, which are included in mass spectrum of the biomolecule X' having the neutral labeled sugar chain and/or information obtained from the mass spectrum of the biomolecule X' but are not included in mass spectrum of the biomolecule Y' having the neutral labeled sugar chain and/or information obtained from the mass spectrum of the biomolecule Y', (b) mass spectrum peaks or information having the same mass/charge and different in ion intensities, which are detected at stronger ion intensity, in mass spectrum of the biomolecule X' having the neutral labeled sugar chain and/or information obtained from the mass spectrum of the biomolecule X', than in mass spectrum of the biomolecule Y' having the neutral labeled sugar chain and/or information obtained from the mass spectrum of biomolecule Y';and (6) determining the structure involved in expression of the particular disease or the structure of the biomolecule X as a structure of disease marker based on the mass spectrum peaks or information picked up in (5).

13. The method for screening disease marker according to claim 11, wherein the biomolecule is a sugar chain.

14. The method for screening disease marker according to claim 11, wherein the particular disease is cancer, and the biomolecule is blood group antigen.

15. The method for screening disease marker according to claim 11, wherein the particular disease is a disease caused by an autoimmune disease and having correlation with blood group, and the biomolecule is blood group antigen.

16. The method for screening disease marker according to claim 11, wherein the particular disease is heart disease or hypercholesterolemia, and the biomolecule is blood group antigen.

17. The method for screening disease marker according to claim 11, wherein the labeling compound used for conducting the labeling is selected from the group consisting of pyrenebutanoic acid hydrazide, aminopyrene, 2-aminopyridine, 2-aminobenzene, and amino benzoic acid ester.

18. The method according to claim 1, wherein the labeling compound is selected from the group consisting of amino pyrene, amino benzene, amino pyridine, pyrene carboxylic acid hydrazide, benzene carboxylic acid hydrazide, and pyridine carboxylic acid hydrazide.

19. The method according to claim 1, wherein the negative ion MALDI analysis is selected from the group consisting of ISD, PSD, and $MS^n$ measurement.

20. A method for screening disease marker, comprising the steps of:

(1) preparing a sample containing a biomolecule X having a neutral sugar chain to be analyzed derived from a subject affected by a particular disease;

labeling the neutral sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule X' having a neutral labeled sugar chain;

wherein the neutral sugar chain contains fucose;

subjecting the biomolecule X' having the neutral labeled sugar chain to negative ion MALDI analysis selected from the group consisting of ISD, PSD, and $MS^n$ measurement, (2) separately, preparing a sample containing a biomolecule Y having the neutral sugar chain to be analyzed derived from a subject unaffected by the particular disease;

labeling the neutral sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule Y' having a neutral labeled sugar chain;

wherein the neutral sugar chain contains fucose;

subjecting the biomolecule Y' having the neutral labeled sugar chain to negative ion MALDI analysis selected from the group consisting of ISD, PSD, and $MS^n$ measurement; or (1) preparing a sample containing a biomolecule X having an acidic sugar chain to be analyzed derived from a subject affected by a particular disease;

neutralizing and labeling the acidic sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule X' having a neutral labeled sugar chain;

wherein the acidic sugar chain contains sialic acid;
subjecting the biomolecule X' having the neutral labeled sugar chain to negative ion MALDI analysis selected from the group consisting of ISD, PSD, and MS" measurement;
(2) separately, preparing a sample containing a biomolecule Y having the acidic sugar chain to be analyzed derived from a subject unaffected by the particular disease;
neutralizing and labeling the acidic sugar chain with a labeling compound having a fundamental skeleton of aromatic selected from the group consisting of pyrene, benzene, and pyridine and comprising at least one selected from the group consisting of amino group and carboxylic acid hydrazide group to obtain a biomolecule Y' having a neutral labeled sugar chain;
wherein the acidic sugar chain contains sialic acid;
subjecting the biomolecule Y' having the neutral labeled sugar chain to negative ion MALDI analysis selected from the group consisting of ISD, PSD, and MS" measurement; and
(3) comparing mass spectrum of the biomolecule X' having the neutral labeled sugar chain obtained in (1) and/or information obtained from the mass spectrum, with mass spectrum of the biomolecule Y' having the neutral labeled sugar chain obtained in (2) and/or information obtained from the mass spectrum, to find mass spectrum peaks and/or information which are mutually different, thereby ascertaining presence of a structure involved in expression of the particular disease.

* * * * *